(12) United States Patent
Cecere et al.

(10) Patent No.: US 10,316,036 B2
(45) Date of Patent: Jun. 11, 2019

(54) SUBSTITUTED PYRAZINO[2,2-A]ISOQUINOLINE DERIVATIVES

(71) Applicant: Hoffmann-La Roche Inc., Little Falls, NJ (US)

(72) Inventors: Giuseppe Cecere, Basel (CH); Guido Galley, Rheinfelden (DE); Roger Norcross, Olsberg (CH); Angelique Patiny-Adam, Rosenau (FR); Philippe Pflieger, Schwoben (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/788,589

(22) Filed: Oct. 19, 2017

(65) Prior Publication Data
US 2018/0037582 A1    Feb. 8, 2018

Related U.S. Application Data

(60) Division of application No. 15/427,373, filed on Feb. 8, 2017, now Pat. No. 9,828,374, which is a continuation of application No. PCT/EP2015/069309, filed on Aug. 24, 2015.

(30) Foreign Application Priority Data

Aug. 27, 2014   (EP) .................................. 14182460

(51) Int. Cl.
C07D 471/04    (2006.01)
A61K 31/4738   (2006.01)

(52) U.S. Cl.
CPC ........ C07D 471/04 (2013.01); A61K 31/4738 (2013.01)

(58) Field of Classification Search
CPC .................................................... C07D 471/04
See application file for complete search history.

*Primary Examiner* — Brian E McDowell
(74) *Attorney, Agent, or Firm* — Brian L. Buckwalter

(57) ABSTRACT

The present invention relates to compounds of formula of formula I wherein R, $R^1$, $R^2$ and L are as described herein, compositions containing compounds of formula I, methods of manufacture of compounds of formula I and methods of treating psychiatric, metabolic, cardiovascular or sleep disorders with compounds of formula I.

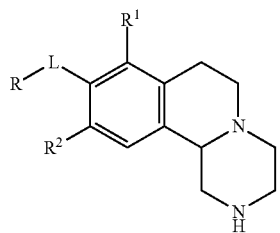

8 Claims, No Drawings

SUBSTITUTED PYRAZINO[2,2-A]ISOQUINOLINE DERIVATIVES

CROSS REFERENCE TO RELATED APPLICATIONS

This application is a continuation application of U.S. Ser. No. 15/427,373 filed Feb. 8, 2017 which is a continuation of International Application No. PCT/EP2015/069309 having an international filing date of Aug. 24, 2015 and which claims benefit under 35 U.S.C. § 119 to European Patent Application No. 14182460.7 filed Aug. 27, 2014. The entire contents of all are incorporated herein by reference.

FIELD OF THE INVENTION

The present invention relates to novel compounds of formula I, as described herein, having pharmaceutical activity, their manufacture, pharmaceutical compositions containing them and their potential use as medicaments.

BACKGROUND OF THE INVENTION

Aberrant activity of Trace Amine Associated Receptors (TAARs), especially for TAAR1 is associated with psychiatric conditions such as depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors. Objects of the present invention show selectivity for TAAR1 receptor over adrenergic receptors, in particular good selectivity vs the human and rat alpha1 and alpha2 adrenergic receptors.

The classical biogenic amines (serotonin, norepinephrine, epinephrine, dopamine, histamine) play important roles as neurotransmitters in the central and peripheral nervous system (Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press). Their synthesis and storage, as well as their degradation and reuptake after release are tightly regulated. An imbalance in the levels of biogenic amines is known to be responsible for the altered brain function under many pathological conditions (Wong, M. L. and Licinio, J. Research and treatment approaches to depression, *Nat. Rev. Neurosci.* 2001 2:343-351; Carlsson, A. et al., Interactions between monoamines, glutamate, and GABA in schizophrenia: new evidence, *Annu. Rev. Pharmacol. Toxicol.* 2001 41:237-260; Tuite, P. and Riss, J., Recent developments in the pharmacological treatment of Parkinson's disease. *Expert Opin. Investig. Drugs* 2003 12:1335-1352, Castellanos, F. X. and Tannock, R., Neuroscience of attention-deficit/hyperactivity disorder: the search for endophenotypes, *Nat. Rev. Neurosci.* 2002 3:617-628). A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines (Usdin, Earl; Sandler, Merton; Editors. *Psychopharmacology Series, Vol. 1: Trace Amines and the Brain.* [*Proceedings of a Study Group at the 14th Annual Meeting of the American College of Neuropsychoparmacology*, San Juan, Puerto Rico] (1976)). Their dysregulation has been linked to various psychiatric diseases like schizophrenia and depression (Lindemann, L. and Hoener, M., A renaissance in trace amines inspired by a novel GPCR family, *Trends in Pharmacol. Sci.* 2005 26:274-281) and for other conditions like attention deficit hyperactivity disorder, migraine headache, Parkinson's disease, substance abuse and eating disorders (Branchek, T. A. and Blackburn, T. P., Trace amine receptors as targets for novel therapeutics: legend, myth and fact, *Curr. Opin. Pharmacol.* 2003 3:90-97; Premont, R. T. et al., Following the trace of elusive amines, *Proc. Natl. Acad. Sci. U.S.A.* 2001 98:9474-9475).

For a long time, TA-specific receptors had only been hypothesized based on anatomically discrete high-affinity TA binding sites in the CNS of humans and other mammals (Mousseau, D. D. and Butterworth, R. F., A high-affinity [3H] tryptamine binding site in human brain. *Prog. Brain Res.* 1995 106:285-291; McCormack, J. K. et al., Autoradiographic localization of tryptamine binding sites in the rat and dog central nervous system. *J. Neurosci.* 1986 6:94-101). Accordingly, the pharmacological effects of TAs were believed to be mediated through the well-known machinery of classical biogenic amines, by either triggering their release, inhibiting their reuptake or by "crossreacting" with their receptor systems (Premont, R. T. et al., Following the trace of elusive amines, *Proc. Natl. Acad. Sci. U.S.A.* 2001 98, 9474-9475; Dyck, L. E., Release of some endogenous trace amines from rat striatal slices in the presence and absence of a monoamine oxidase inhibitor. *Life Sci.* 1989 44, 1149-1156; Parker, E. M. and Cubeddu, L. X. (1988) Comparative effects of amphetamine, phenylethylamine and related drugs on dopamine efflux, dopamine uptake and mazindol binding, *J. Pharmacol. Exp. Ther.* 1989 245, 199-210). This view changed significantly with the recent identification of several members of a novel family of GPCRs, the trace amine associated receptors (TAARs). There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison, and pharmacological data suggest that these receptors form three distinct subfamilies (Lindemann, L. and Hoener, M. (2005) A renaissance in trace amines inspired by a novel GPCR family, *Trends in Pharmacol. Sci.* 26, 274-281; Lindemann, L. et al. (2005) Trace amine associated receptors form structurally and functionally distinct subfamilies of novel G protein-coupled receptors, *Genomics* 2005 85:372-385). TAAR1 is in the first subclass of four genes (TAAR1-4) highly conserved between human and rodents. TAs activate TAAR1 via Gαs. Dysregulation of TAs was shown to contribute to the etiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

BRIEF SUMMARY OF THE INVENTION

The invention relates to compounds of formula I

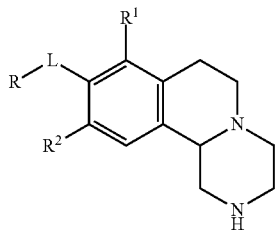

wherein
$R^1/R^2$ are independently from each other hydrogen or halogen;
L is a bond, —NH—, —C(O)NH—, —NHC(O)— or NHC(O)NH—;
R is hydrogen, halogen, lower alkyl, cycloalkyl, benzyl, phenyl or a five or six membered heteroaryl group, wherein phenyl and the heteroaryl groups are optionally substituted by one or two substituents, selected from halogen, lower alkyl, lower alkoxy, lower alkyl substituted by halogen, lower alkoxy substituted by halogen, cycloalkyl or di-lower alkyl amino provided that if R is halogen, then L is a bond.
or to a pharmaceutically suitable acid addition salt thereof, to all racemic mixtures, all their corresponding enantiomers and/or optical isomers.

In another embodiment, the present inventions provide for pharmaceutical compositions comprising compounds of Formula I.

In another embodiment, the present invention provides for methods of treating disease associated with trace amine associated receptors.

DETAILED DESCRIPTION OF THE INVENTION

Objects of the present invention are new compounds of formula I and their pharmaceutically acceptable salts, their use for the manufacture of medicaments for the treatment of diseases related to the biological function of the trace amine associated receptors, their manufacture and medicaments based on a compound in accordance with the invention in the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety, attention deficit hyperactivity disorder (ADHD) and diabetes.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group wherein the alkyl residue is as defined above and which is attached via an oxygen atom.

The term "halogen" denotes chlorine, iodine, fluorine and bromine. The preferred halogen groups are fluorine or chlorine.

As used herein, the term "lower alkyl substituted by halogen" denotes a saturated straight- or branched-chain group containing from 1 to 7 carbon atoms as defined for the term "lower alkyl", wherein at least one hydrogen atom is replaced by a halogen atom. A preferred halogen atom is fluoro. Examples of such groups are $CF_3$, $CHF_2$, $CH_2F$, $CH_2CF_3$ or $CH_2CHF_2$.

As used herein, the term "lower alkoxy substituted by halogen" denotes an alkoxy group as defined above, and wherein at least one hydrogen atom is replaced by halogen.

The term "cycloalkyl" denotes a saturated carbon ring, containing from 3 to 6 carbon atoms, for example cyclopropyl, cyclobutyl, cyclopentyl or cyclohexyl.

The term "five or six membered heteroaryl group" denotes a cyclic aromatic 5 or 6 membered ring, wherein at least one carbon atom is replaced by a nitrogen atom, for example the groups pyridinyl, pyrimidinyl, pyrazolyl, pyrazinyl, oxadiazolyl or thiadiazolyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, 2,2,2-trifluoroacetic acid, succinic acid, tartaric acid, methane-sulfonic acid, p-toluenesulfonic acid and the like.

One embodiment of the invention are compounds of formula I, in which L is a bond and R is hydrogen, lower alkyl, cycloalkyl or halogen, for example the following compounds (11bR)-9-bromo-2,3,4,6,7,11b-hexahydro-1H-pyrazino[2,1-a]isoquinoline (11bR)-2,3,4,6,7,11b-hexahydro-1H-pyrazino[2,1-a]isoquinoline (11bR)-9-ethyl-2,3,4,6,7,11b-hexahydro-1H-pyrazino[2,1-a]isoquinoline (11bR)-9-methyl-2,3,4,6,7,11b-hexahydro-1H-pyrazino[2,1-a]isoquinoline (11bR)-9-cyclopropyl-2,3,4,6,7,11b-hexahydro-1H-pyrazino[2,1-a]isoquinoline (11bR)-8-fluoro-2,3,4,6,7,11b-hexahydro-1H-pyrazino[2,1-a]isoquinoline One further embodiment of the invention are compounds of formula I, in which L is —NH—, for example the following compounds
(11bR)—N-[2-(trifluoromethyl)pyrimidin-4-yl]-2,3,4,6,7,11b-hexahydro-1H-pyrazino[2,1-a]isoquinolin-9-amine
(11bR)—N-[5-(trifluoromethyl)pyrimidin-2-yl]-2,3,4,6,7,11b-hexahydro-1H-pyrazino[2,1-a]isoquinolin-9-amine
(11bR)—N-[5-(trifluoromethyl)pyrazin-2-yl]-2,3,4,6,7,11b-hexahydro-1H-pyrazino[2,1-a]isoquinolin-9-amine
(11bS)—N-[2-(trifluoromethyl)pyrimidin-4-yl]-2,3,4,6,7,11b-hexahydro-1H-pyrazino[2,1-a]isoquinolin-9-amine
(11bS)—N-[5-(trifluoromethyl)pyrazin-2-yl]-2,3,4,6,7,11b-hexahydro-1H-pyrazino[2,1-a]isoquinolin-9-amine
(R)—N-(5-(2,2,2-trifluoroethoxy)pyrimidin-2-yl)-2,3,4,6,7,11b-hexahydro-1H-pyrazino[2,1-a]isoquinolin-9-amine (11bR)—N-(5-cyclopropylpyrimidin-2-yl)-2,3,4,6,7,11b-hexahydro-1H-pyrazino[2,1-a]isoquinolin-9-amine
(11bR)-10-fluoro-N-[5-(trifluoromethyl)pyrimidin-2-yl]-2,3,4,6,7,11b-hexahydro-1H-pyrazino[2,1a]isoquinolin-9-amine
(11bR)—N-[6-methoxy-2-(trifluoromethyl)pyrimidin-4-yl]-2,3,4,6,7,11b-hexahydro-1H-pyrazino[2,1-a]isoquinolin-9-amine
N4-[(11bR)-2,3,4,6,7,11b-hexahydro-1H-pyrazino[2,1-a]isoquinolin-9-yl]-N6,N6-dimethyl-2-(trifluoromethyl)pyrimidine-4,6-diamine
(11bR)—N-[6-methyl-2-(trifluoromethyl)pyrimidin-4-yl]-2,3,4,6,7,11b-hexahydro-1H-pyrazino[2,1-a]isoquinolin-9-amine
(11bR)—N-[6-chloro-2-(trifluoromethyl)pyrimidin-4-yl]-2,3,4,6,7,11b-hexahydro-1H-pyrazino[2,1a]isoquinolin-9-amine
(11bR)—N-pyrimidin-2-yl-2,3,4,6,7,11b-hexahydro-1H-pyrazino[2,1-a]isoquinolin-9-amine
(11bR)—N-(2,6-dimethylpyrimidin-4-yl)-2,3,4,6,7,11b-hexahydro-1H-pyrazino[2,1-a]isoquinolin-9-amine
(11bR)—N-[4-(trifluoromethyl)pyrimidin-2-yl]-2,3,4,6,7,11b-hexahydro-1H-pyrazino[2,1-a]isoquinolin-9-amine
(11bR)—N-(5-ethylpyrimidin-2-yl)-2,3,4,6,7,11b-hexahydro-1H-pyrazino[2,1-a]isoquinolin-9-amine
(R)—N-(6-methyl-2-(2,2,2-trifluoroethoxy)pyrimidin-4-yl)-2,3,4,6,7,11b-hexahydro-1H-pyrazino[2,1-a]isoquinolin-9-amine
(11bS)—N-[6-chloro-2-(trifluoromethyl)pyrimidin-4-yl]-8-fluoro-2,3,4,6,7,11b-hexahydro-1H-pyrazino[2,1-a]isoquinolin-9-amine
(11bR)—N-(5-cyclopropylpyrimidin-2-yl)-8-fluoro-2,3,4,6,7,11b-hexahydro-1H-pyrazino[2,1-a]isoquinolin-9-amine
(11bR)—N-[6-chloro-2-(trifluoromethyl)pyrimidin-4-yl]-8-fluoro-2,3,4,6,7,11b-hexahydro-1H-pyrazino[2,1a]isoquinolin-9-amine
N-[(11R)-2,3,4,6,7,11-hexahydro-1H-pyrazino[2,1-a]isoquinolin-9-yl]-3-cyclopropyl-1,2,4-oxadiazol-5-amine
(R)—N-(2,3,4,6,7,11b-hexahydro-1H-pyrazino[2,1-a]isoquinolin-9-yl)-3-methyl-1,2,4-thiadiazol-5-amine or
(11bR)-2,3,4,6,7,11b-hexahydro-1H-pyrazino[2,1-a]isoquinolin-9-amine.

One further embodiment of the invention are compounds of formula I, in which L is —C(O)NH—, for example the following compounds
N-[(11bR)-2,3,4,6,7,11b-hexahydro-1H-pyrazino[2,1-a]isoquinolin-9-yl]-2-(trifluoromethyl)pyridine-4-carboxamide
N-[(11bR)-2,3,4,6,7,11b-hexahydro-1H-pyrazino[2,1-a]isoquinolin-9-yl]-4-chloro-benzamide
N-[(11bR)-2,3,4,6,7,11b-hexahydro-1H-pyrazino[2,1-a]isoquinolin-9-yl]-2-(trifluoromethyl)pyrimidine-5-carboxamide
N-[(11bS)-2,3,4,6,7,11b-hexahydro-1H-pyrazino[2,1-a]isoquinolin-9-yl]-4-chloro-benzamide
N-[(11bS)-2,3,4,6,7,11b-hexahydro-1H-pyrazino[2,1-a]isoquinolin-9-yl]-2-(trifluoromethyl)pyridine-4-carboxamide
N-[(11bS)-2,3,4,6,7,11b-hexahydro-1H-pyrazino[2,1-a]isoquinolin-9-yl]-2-(trifluoromethyl)pyrimidine-5-carboxamide
N-[(11bR)-10-fluoro-2,3,4,6,7,11b-hexahydro-1H-pyrazino[2,1-a]isoquinolin-9-yl]-2-(trifluoromethyl)pyridine-4-carboxamide
N-[(11bR)-8-fluoro-2,3,4,6,7,11b-hexahydro-1H-pyrazino[2,1-a]isoquinolin-9-yl]-2-(trifluoromethyl)pyridine-4-carboxamide
(R)—N-(2,3,4,6,7,11b-hexahydro-1H-pyrazino[2,1-a]isoquinolin-9-yl)-6-methyl-2-(trifluoromethyl)pyrimidine-4-carboxamide
(R)—N-(2,3,4,6,7,11b-hexahydro-1H-pyrazino[2,1-a]isoquinolin-9-yl)-3-isopropyl-1-methyl-1H-pyrazole-5-carboxamide or
(R)-3-ethyl-N-(2,3,4,6,7,11b-hexahydro-1H-pyrazino[2,1-a]isoquinolin-9-yl)-4-methyl-1H-pyrazole-5-carboxamide.

One further embodiment of the invention are compounds of formula I, in which L is —NHC(O)—, for example the following compounds
(11bR)—N-(6-chloro-3-pyridyl)-2,3,4,6,7,11b-hexahydro-1H-pyrazino[2,1-a]isoquinoline-9-carboxamide
(11bR)—N-[[3-(trifluoromethyl)phenyl]methyl]-2,3,4,6,7,11b-hexahydro-1H-pyrazino[2,1-a]isoquinoline-9-carboxamide
(11bR)—N-(4-chlorophenyl)-2,3,4,6,7,11b-hexahydro-1H-pyrazino[2,1-a]isoquinoline-9-carboxamide
(11bR)—N-(6-methoxy-3-pyridyl)-2,3,4,6,7,11b-hexahydro-1H-pyrazino[2,1-a]isoquinoline-9-carboxamide or
(11bR)—N-(2-chloropyrimidin-5-yl)-2,3,4,6,7,11b-hexahydro-1H-pyrazino[2,1-a]isoquinoline-9-carboxamide.

One further embodiment of the invention are compounds of formula I, in which L is —NHC(O)NH—, for example the following compounds
(R)-1-(2,3,4,6,7,11b-hexahydro-1H-pyrazino[2,1-a]isoquinolin-9-yl)-3-(4-(trifluoromethyl)phenyl)urea or
(R)-1-(2,3,4,6,7,11b-hexahydro-1H-pyrazino[2,1-a]isoquinolin-9-yl)-3-(4-methoxyphenyl)urea.

The preparation of compounds of formula I of the present invention may be carried out in sequential or convergent synthetic routes. Syntheses of the compounds of the invention are shown in the following schemes 1-5 and in the description of 47 specific examples. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1-5, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods known in the art, for example, by processes described below, which process comprises a) cleaving off the N-protecting group (PG) from compounds of formula

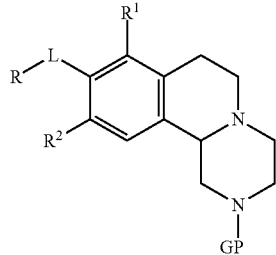

II to a compound of formula

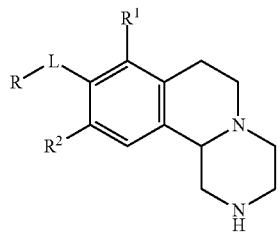

I wherein PG is a N-protecting group selected from —C(O)O-tert-butyl and the other definitions are as described above, and, if desired, converting the compounds obtained into pharmaceutically acceptable acid addition salts.

General Procedure

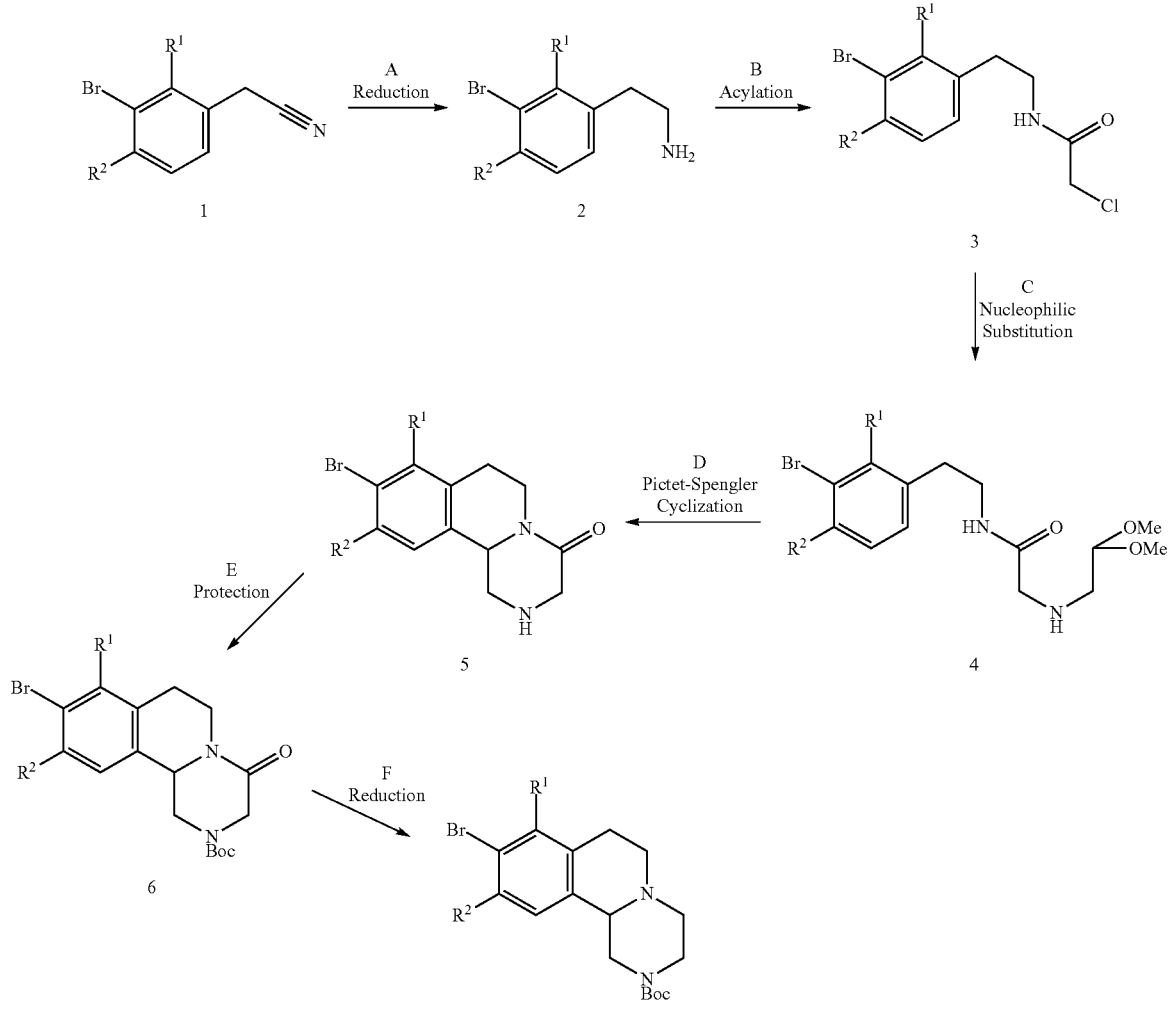

wherein the substituents $R^1$ and $R^2$ are described above.

Step A:

In cases where 2-aryl ethanamine 2 is not commercially available, it may be prepared by treatment of the corresponding nitrile 1 with a reducing agent such as LiAlH$_4$ or BH$_3$.THF in a solvent such as THF, 1,4-dioxane, ether or TBME.

Preferred conditions are BH$_3$.THF in THF at 0° C. to room temperature followed by reflux in a 1:2 mixture of MeOH/THF.

Step B:

Acylation of 2-aryl ethanamine 2 can be accomplished by treatment with chloroacetyl chloride [CAS 79-04-9], in the presence of an inorganic base such as NaHCO$_3$, KHCO$_3$, Na$_2$HPO$_4$ or NaH$_2$PO$_4$, in halogenated solvents such as dichloromethane or 1,2-dichloroethane or ethereal solvents such as diethyl ether, dioxane, THF or TBME.

Preferred conditions are NaHCO$_3$ in dichloromethane for 1 h at 0° C. then at room temperature for 16 hours.

Step E:

Protection of the secondary amine in tricycle compound 5 can be effected by treatment with di-tert-butyl carbonate, optionally in the presence of an organic base such as triethylamine, N,N-diisopropylethylamine or N-methylmorpholine, in halogenated solvents such as dichloromethane or 1,2-dichloroethane or ethereal solvents such as diethyl ether, dioxane, THF or TBME or protic solvents such as MeOH or EtOH.

Preferred conditions are dichloromethane in the presence of triethylamine at room temperature for 16 hours.

If desired, the racemic mixture of chiral N-Boc protected pyrazinoisoquinoline 6 may be separated into its constituent enantiomers by using chiral HPLC.

Step F:

Reduction of amide 6 to desired tricycle derivative 7 can be accomplished by treatment with a reducing agent such as DIBAL-H, LiAlH$_4$ or BH$_3$.THF in a solvent such as dichloromethane, THF, 1,4-dioxane, ether or TBME.

Preferred conditions are BH$_3$.THF in THF at room temperature for 16 hour.

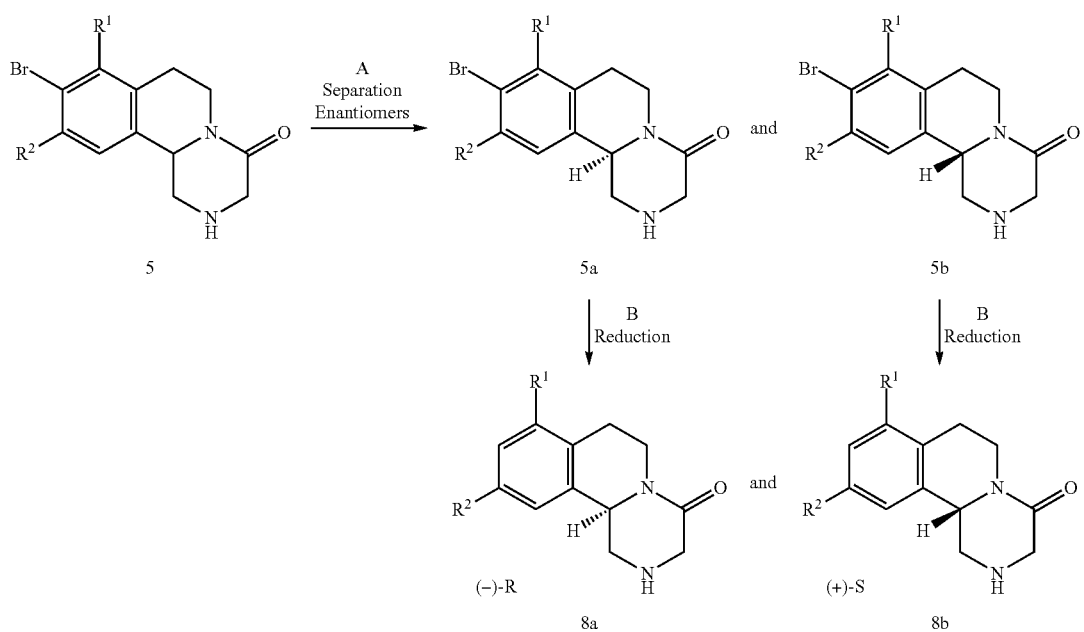

Scheme 2

Step C:

Nucleophilic substitution between electrophile chloride 3 and aminoacetaldehyde dimethyl acetal [CAS 22483-09-6] can be performed in absence of a base in a non-protic organic solvent such as diethyl ether, THF, toluene, 1,4-dioxane or TBME, preferably at elevated temperatures.

Preferred conditions are using excess of aminoacetaldehyde dimethyl acetal in toluene at reflux for 2 hours.

Step D:

Cyclization of intermediate amine 4 to pyrazinoisoquinoline 5 can be accomplished by an acid-mediated Pictet-Spengler reaction using conc. H$_2$SO$_4$, optionally with dichloromethane as co-solvent, according to a modification of the procedure previously reported by Kim and co-workers (*Tetrahedron*, 1998, 54, 7395-7400).

Preferred conditions are using a 1:2 mixture of H$_2$SO$_4$/CH$_2$Cl$_2$ at 5° C. for 1 hour then to room temperature for 4 hours.

wherein the substituents R$^1$ and R$^2$ are hydrogen and 8a and 8b can be further reacted as described for compound 5 in Scheme 1.

Step A:

Enantiomers of 5 (5a and 5b) can be separated using chiral HPLC. Preferred conditions are using SFC (Column: Chiralpak AD-3, 100×4.6 mm I.D., 3 μm) with ethanol+0.05% DEA in CO$_2$ using a 5% to 40% gradient.

Step B:

Removal of the bromine in 5a and 5b can be effected by hydrogenolysis of C—Br bond with hydrogen under normal or elevated pressure or by transfer hydrogenation using ammonium formate or cyclohexadiene as hydrogen source in the presence of a palladium catalyst in solvents such as MeOH, EtOH, H$_2$O, dioxane, THF, HOAc, EtOAc, DMF or mixtures thereof.

Preferred conditions are palladium on charcoal in MeOH at room temperature and 1 atm H$_2$ for 4 hours.

Absolute configurational assignment of 5a and 5b was based on spectroscopic data and optical rotation comparison with identical literature reference compounds (Cedillo-Cruz and co-workers, *Tetrahedron: Asymmetry*, 2014, 25, 133-140).
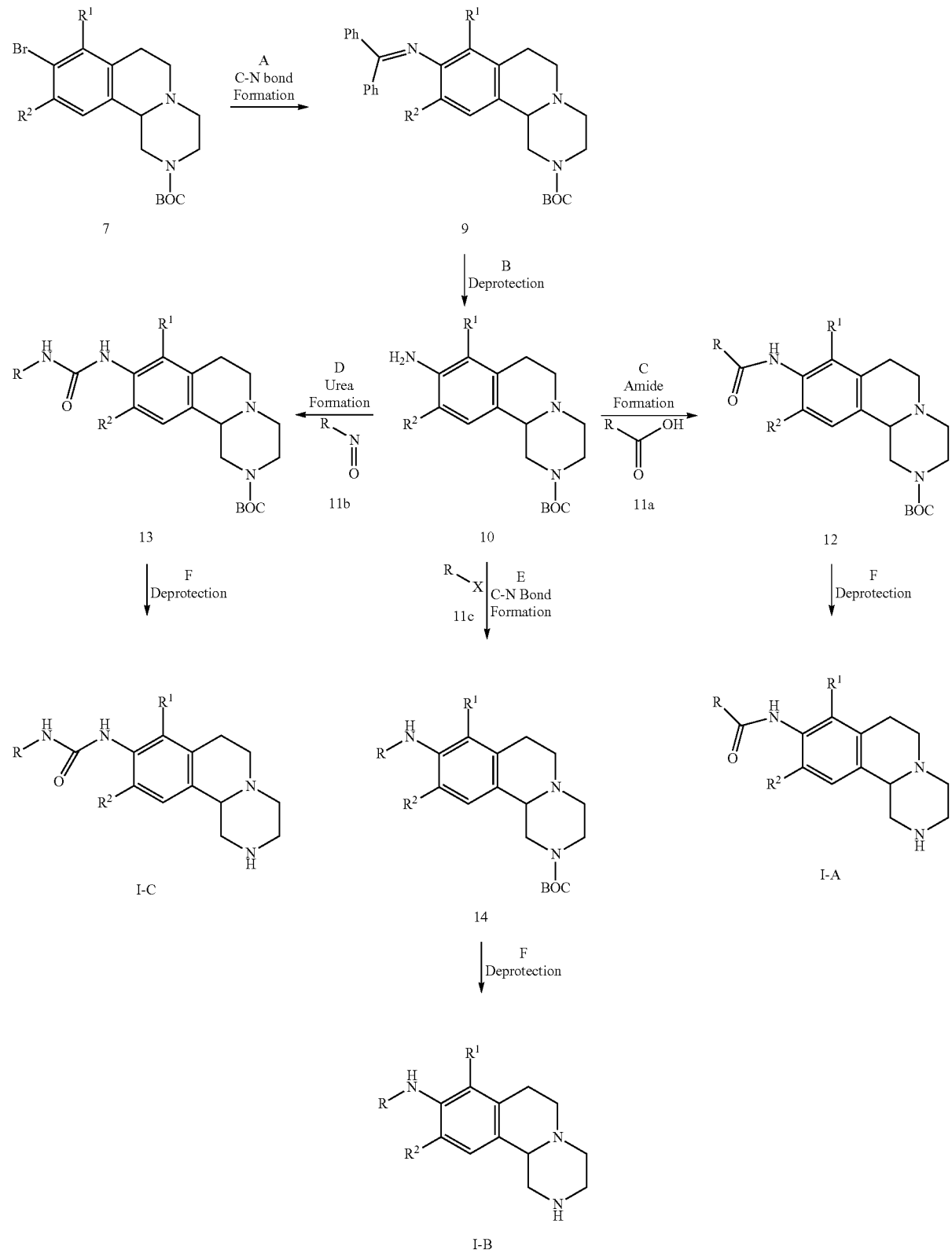
Scheme 3 wherein the substituents $R^1$ and $R^2$ are as described above and R is benzyl, phenyl or a five or six membered heteroaryl group, wherein phenyl and the heteroaryl groups are optionally substituted by one or two substituents, selected from halogen, lower alkyl, lower alkoxy, lower alkyl substituted by halogen, lower alkoxy substituted by halogen, cycloalkyl or di-lower alkyl amino; are described above; X is halogen.

Step A:

C—N bond formation can be accomplished by treatment of 7 with benzophenone imine [CAS 1013-88-3] in the presence of a palladium or copper catalyst, a ligand and a base in solvents such as 1,4-dioxane, DME, THF, toluene, DMF and DMSO at elevated temperatures, for instance using a palladium-catalysed Buchwald-Hartwig reaction.

Preferred conditions are catalytic tris(dibenzylidineacetone) dipalladium(0), catalytic rac-2,2'-bis(diphenylphosphino)-1,1'-binaphthyl and sodium tert-butoxide in toluene at 100° C. for 3 hour.

Step B:

Removal of N-diphenylmethylene group can be accomplished by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, 1,4-dioxane, THF, EtOAc, dichloromethane, chloroform, DMF or mixture thereof.

The transformation can also be effected by treatment with hydroxylamine hydrochloride, together with a base such as sodium acetate, potassium acetate, sodium carbonate, potassium carbonate, cesium carbonate in solvents such as MeOH, EtOH, 1,4-dioxane, THF, DMF or mixture thereof.

Preferred conditions are hydroxylamine hydrochloride, together with sodium acetate, in MeOH at 50° C. for 16 hour.

Step C:

Amide formation can be accomplished by a coupling reaction between aniline 10 and a carboxylic acid 11a with a coupling reagent such as DCC, EDC, TBTU, HBTU or HATU in the presence of an organic base such as triethylamine, N,N-diisopropylethylamine or N-methylmorpholine in solvents such as dichloromethane, 1,2-dichloroethane, DMF, DMSO, or ethereal solvents including diethyl ether, 1,4-dioxane, THF, DME, or TBME.

Preferred conditions are HBTU with N-methylmorpholine in DMF at room temperature for 16 hours.

Step D:

Urea formation can be accomplished by a coupling reaction between aniline 10 and an isocyanate 11b, optionally in the presence of an organic base such as triethylamine, N,N-diisopropylethylamine or N-methylmorpholine in halogenated solvents such as dichloromethane, 1,2-dichloroethane, chlorobenzene or protic solvents such as DMF, NMP, DMA or ethereal solvents such as diethyl ether, 1,4-dioxane, THF, DME or TBME.

Preferred conditions are in absence of base in THF at 30-60° C. for 16-24 hours.

Step E:

Coupling reaction between aryl halide 11c and aniline 10 can be accomplished by using a palladium or copper catalyst, a ligand, and a base in solvents such as 1,4-dioxane, DMF, THF, toluene, DMF and DMSO at elevated temperatures, for instance using a palladium-catalysed Buchwald-Hartwig reaction.

Preferred conditions are catalytic tris(dibenzylidineacetone) dipalladium(0), catalytic 4,5-bis(diphenylphosphino)-9,9-dimethylxanthene (Xantphos), $Cs_2CO_3$ in 1,4-dioxane at 95° C. for 16 hours.

Alternatively, in case the aryl halide 11c is activated toward undergoing aromatic nucleophilic substitution due to the presence of electron withdrawing substituents, the coupling reaction can be accomplished by heating aryl halide 11c and aniline 10 in solvents such as DMF, DMSO, NMP, DMA in the presence of an organic base such as triethylamine, N,N-diisopropylethylamine or N-methylmorpholine.

Preferred conditions are N,N-diisopropylethylamine in DMA at 100° C. for 16 hours.

Step F:

Removal of the N-Boc protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0-80° C.

Preferred conditions are $CF_3COOH$ in $CH_2Cl_2$ at room temperature for 2 hours or 4.0 M HCl in 1,4-dioxane at 60° C. for 2 hours then allowed to cool to room temperature for 16 hours.

Scheme 4

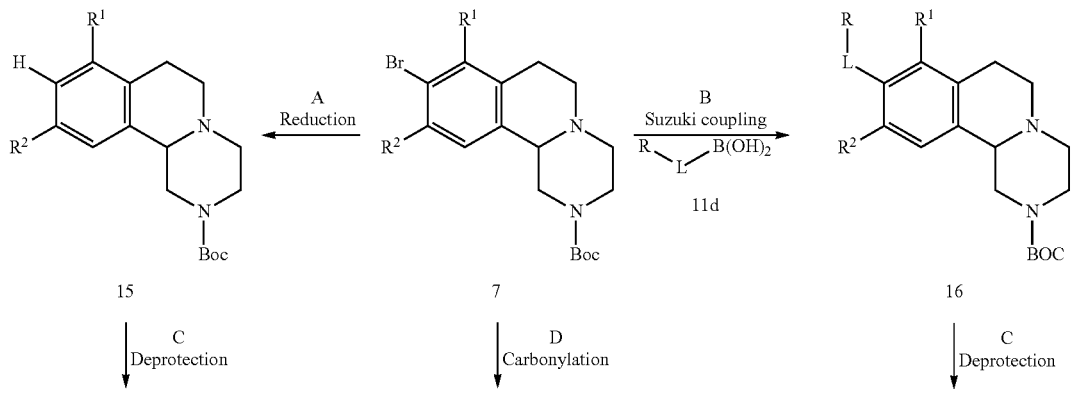

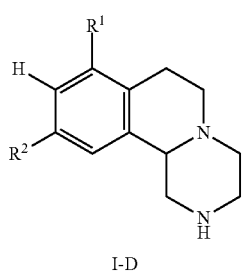 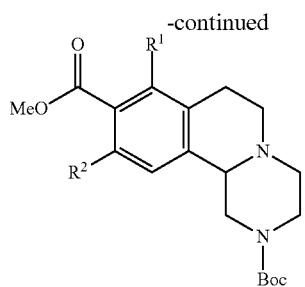 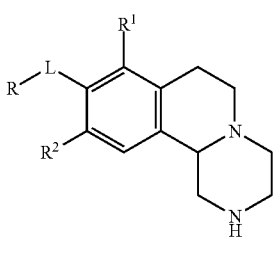

wherein the substituents R² and L are described above and R is lower alkyl or cycloalkyl.

Step A:
Hydrogenolysis of C—Br bond in aryl bromide 7 can be achieved with hydrogen under normal or elevated pressure or by transfer hydrogenation using ammonium formate or cyclohexadiene as hydrogen source in the presence of a palladium catalyst in solvents such as MeOH, EtOH, H₂O, dioxane, THF, HOAc, EtOAc, DMF or mixtures thereof.
Preferred conditions are palladium on charcoal in MeOH at room temperature and 1 atm H₂ for 4 hours.

Step B:
Suzuki-Miyaura coupling between aryl bromide 7 and a suitable boronic acid 11d can be carried out with a palladium catalyst, a phosphine ligand, and a base such as triethylamine, diisopropylethylamine, K₂CO₃, Na₂CO₃, Cs₂CO₃, K₂HPO₄, KO$^t$Bu, in solvents such as DMF, acetonitrile, DMSO, THF, DME, toluene, 1,4-dioxane, H₂O or mixture thereof, at room temperature to elevated temperatures.
Preferred conditions are catalytic Pd(OAc)₂, catalytic tricyclohexylphosphine, K₂HPO₄, in a 20:1 mixture of toluene and H₂O at 100° C. for 8 hours.

Step C:
Removal of the N-Boc protecting group can be effected with mineral acids such as HCl, H₂SO₄ or H₃PO₄ or organic acids such as CF₃COOH, CHCl₂COOH, HOAc or p-toluenesulfonic acid in solvents such as CH₂Cl₂, CHCl₃, THF, MeOH, EtOH or H₂O at 0-80° C.
Preferred conditions are CF₃COOH in CH₂Cl₂ at room temperature for 2 hours or 4.0 M HCl in 1,4-dioxane at 60° C. for 2 hours then allowed to cool to room temperature for 16 hours.

Step D:
Methyl ester 17 can be obtained by a palladium-mediated carbonylation reaction between aryl bromide 7 and CO$_{(g)}$ in MeOH in the presence of an organic base such as triethylamine, N,N-diisopropylethylamine or N-methylmorpholine and a catalytic amount of phosphine ligand.
Preferred conditions are catalytic Pd(OAc)₂, catalytic 1,3-bis(diphenylphosphino)propane [CAS 6737-42-4], triethylamine as base in a 1:1 mixture of MeOH/DMSO at 80° C. for 16 hours.

Scheme 5

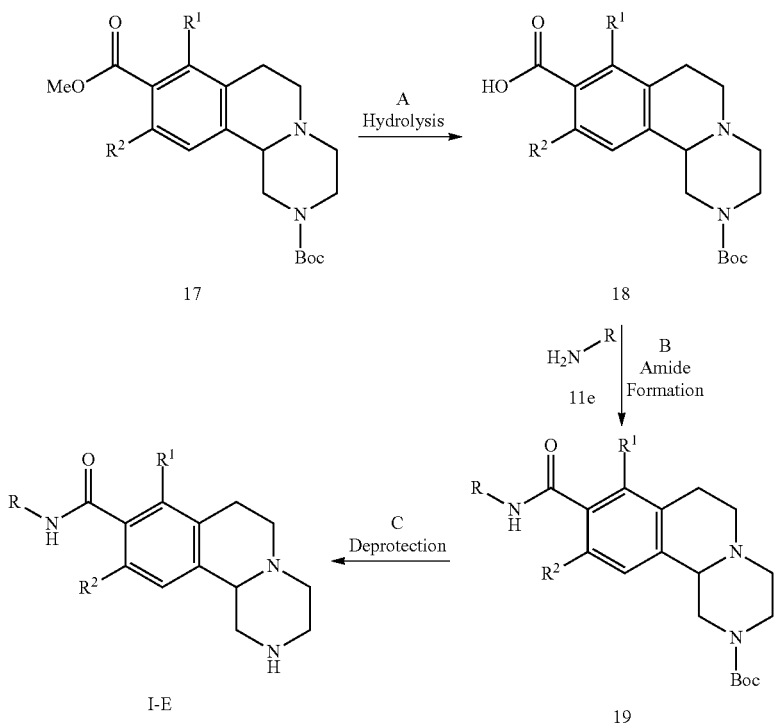

wherein the substituents R² and R are described above.

Step A:

Hydrolysis of methyl ester 17 to carboxylic acid 18 best performed under basic conditions because of the presence of an N-Boc protecting group. Typical conditions involve treatment with an inorganic base such as LiOH, NaOH, KOH, $K_2CO_3$ in a mixture of an organic solvent such as MeOH, EtOH, THF, $CH_3CN$, DMF, DMSO and water at room temperature to elevated temperatures.

Preferred conditions are LiOH in a 1:1 mixture of THF and water at room temperature for 12 hours.

Step B:

Amide formation can be accomplished by a coupling reaction between carboxylic acid 18 and an amine 11e with a coupling reagent such as DCC, EDC, TBTU, HBTU, HATU or $T_3P$ in the presence of an organic base such as triethylamine, N,N-diisopropylethylamine, N-methylmorpholine or pyridine in solvents such as dichloromethane, 1,2-dichloroethane, DMF, DMSO, ethyl acetate or ethereal solvents including diethyl ether, 1,4-dioxane, THF, DME, or TBME.

Preferred conditions are $T_3P$ (n-propanephosphonic acid anhydride) with pyridine in ethyl acetate at room temperature for 16 hours.

Step C:

Removal of the N-Boc protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0-80° C.

Preferred conditions are $CF_3COOH$ in $CH_2Cl_2$ at room temperature for 2 hours or 4.0 M HCl in 1,4-dioxane at 60° C. for 2 hours then allowed to cool to room temperature for 16 hours.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC. Racemic mixtures of chiral synthetic intermediates may also be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, 2,2,2-trifluoro acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

Example 1

N-[(11bR)-2,3,4,6,7,11b-hexahydro-1H-pyrazino[2,1-a]isoquinolin-9-yl]-2-(trifluoromethyl)pyridine-4-carboxamide

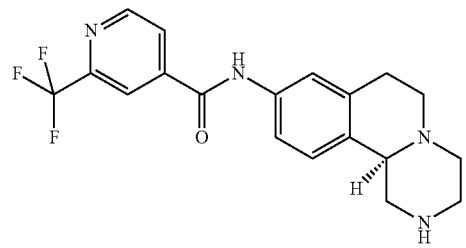 [SMILES: O=C(Nc1ccc2c(c1)CCN1CCNC[C@@H]21)c1ccnc(C(F)(F)F)c1]

a) N-(3-bromophenethyl)-2-chloroacetamide

To a suspension of 2-(3-bromophenyl)ethanamine (10 g, 48.5 mmol, CAS 58971-11-2) and $NaHCO_3$ (4.28 g, 50.9 mmol) in dichloromethane (60 mL) was added dropwise chloroacetyl chloride (4.66 mL, 58.2 mmol, CAS 79-04-9) at 0° C. during 30 min. The reaction mixture was allowed to warm to room temperature overnight, before being quenched by slow addition of water at 0° C. The organic layer was separated, and washed successively with 10% aqueous HCl solution and brine, dried ($Na_2SO_4$), filtered and concentrated in vacuo to afford the title compound (9.38 g) as viscous yellow oil which was used in the next step without further purification.

b) N-(3-bromophenethyl)-2-(2,2-dimethoxyethylamino)acetamide

To a solution of N-(3-bromophenethyl)-2-chloroacetamide (9.38 g, 33.9 mmol) in toluene (20 mL) was added aminoacetaldehyde dimethyl acetal (7.33 mL, 67.8 mmol, CAS 22483-09-6) and the mixture was heated to reflux for 2 hours. After cooling to room temperature, the solvent was evaporated and the residue partitioned between EtOAc and water. The phases were separated and the organic layer was dried over $Na_2SO_4$ and concentrated in vacuo to afford the title compound (11.1 g) as an orange oil which was used in the next step without further purification.

c) (RS)-9-bromo-1,2,3,6,7,11b-hexahydropyrazino[2,1-a]isoquinolin-4-one

To a solution of N-(3-bromophenethyl)-2-(2,2-dimethoxyethylamino)acetamide (2 g, 5.79 mmol) in $CH_2Cl_2$ (4 mL) was added dropwise sulfuric acid (2.01 mL, 37.7 mmol) at 0-5° C. The reaction mixture was allowed to warm up to room temperature for 30 min before being poured into ice-water. The pH was adjusted to 12 by addition of aqueous NaOH (20 wt. %) while cooling. The water phase was extracted with $CH_2Cl_2$ twice. The combined organic extracts were washed with brine, dried ($Na_2SO_4$), filtered and concentrated in vacuo. The residue was purified by flash chromatography (silica gel, gradient 5% to 10% MeOH in CH$_2$Cl$_2$) to afford the title compound (1.31 g, 80% yield) as an orange crystalline solid. MS (ISP): 283.4 ([{$^{81}$Br}M+H]$^+$), 281.4 ([{$^{79}$Br}M+H]$^+$).

d) (11bR)-9-bromo-1,2,3,6,7,11b-hexahydropyrazino[2,1-a]isoquinolin-4-one & (11bS)-9-bromo-1,2,3,6,7,11b-hexahydropyrazino[2,1-a]isoquinolin-4-one The enantiomers of (RS)-9-bromo-1,2,3,6,7,11b-hexahydropyrazino[2,1-a]isoquinolin-4-one were separated using SFC (column: Chiralpak AD-H, 250×20 mm I.D., eluent: 30% methanol with 0.5% Et$_2$NH in 70% CO$_2$) affording:
(−)-(11bR)-9-bromo-1,2,3,6,7,11b-hexahydropyrazino[2,1-a]isoquinolin-4-one (163 mg, light orange oil), retention time=5.29 min
(+)-(11bS)-9-bromo-1,2,3,6,7,11b-hexahydropyrazino[2,1-a]isoquinolin-4-one (119 mg, light orange oil), retention time=8.64 min e) tert-butyl (11bR)-9-bromo-4-oxo-3,6,7,11b-tetrahydro-1H-pyrazino[2,1-a]isoquinoline-2-carboxylate To a stirred solution of (11bR)-9-bromo-1,2,3,6,7,11b-hexahydropyrazino[2,1-a]isoquinolin-4-one (1.27 g, 4.54 mmol) and Et$_3$N (2.21 mL, 15.9 mmol) in CH$_2$Cl$_2$ (30 mL) was added Boc$_2$O (1.19 g, 5.45 mmol) and the mixture was stirred at room temperature for 16 hours. The reaction mixture was partitioned between aqueous citric (10 wt. %) acid and CH$_2$Cl$_2$. The layers were separated and the organic phase was washed with saturated aqueous NaHCO$_3$, dried (Na$_2$SO$_4$) and concentrated in vacuo. The residue was purified by flash column chromatography (silica gel; gradient: 0% to 40% EtOAc in heptane) to afford the title compound (1.41 g, 81%) as a white powder. MS (ISP): 327.4 ([{$^{81}$Br}M+H—C$_4$H$_8$]$^+$), 325.4 ([{$^{79}$Br}M+H—C$_4$H$_8$]$^+$).

f) tert-butyl (11bR)-9-bromo-1,3,4,6,7,11b-hexahydropyrazino[2,1-a]isoquinoline-2-carboxylate To a stirred solution of tert-butyl (11bR)-9-bromo-4-oxo-3,6,7,11b-tetrahydro-1H-pyrazino[2,1-a]isoquinoline-2-carboxylate (1.41 g, 3.7 mmol) in THF (60 mL) was added borane-tetrahydrofuran complex 1.0 M in THF (22.2 mL, 22.2 mmol) and the mixture was stirred at room temperature for 16 hours. The reaction mixture was then poured into saturated aqueous NaHCO$_3$ and extracted twice with EtOAc. The combined organic extracts were washed with saturated brine, dried (Na$_2$SO$_4$) and concentrated in vacuo. The residue was purified by flash column chromatography (silica gel; gradient: 0% to 30% EtOAc in heptane) to afford the title compound (1.1 g, 81%) as a white powder MS (ISP): 369.5 ([{$^{81}$Br}M+H]$^+$), 367.5 ([{$^{79}$Br}M+H]$^+$).

g) tert-butyl (11bR)-9-(benzhydrylideneamino)-1,3,4,6,7,11b-hexahydropyrazino[2,1-a]isoquinoline-2-carboxylate A screw-cap vial was charged with tert-butyl (11bR)-9-bromo-1,3,4,6,7,11b-hexahydropyrazino[2,1-a]isoquinoline-2-carboxylate (100 mg, 0.272 mmol), benzophenone imine (104 mg, 0.545 mmol, CAS 1013-88-3), (rac)-2,2'-bis(diphenylphosphino)-1,1'-binaphthyl (17.0 mg, 0.027 mmol), tris(dibenzylideneacetone)dipalladium(0) (7.48 mg, 8.17 µmol) and sodium tert-butoxide (41.9 mg, 0.436 mmol). The vial was then degassed by alternative evacuation and back filling with argon. Toluene (1.5 mL) was added and the resulting mixture was flushed with a stream of argon for 10 min. The reaction mixture was heated to 90° C. in an oil bath for 3 hours then filtered directly through a plug of dicalite. The filter cake was rinsed with EtOAc and the filtrate was washed with brine, dried (Na$_2$SO$_4$) and concentrated in vacuo. The residue was purified by flash column chromatography (silica gel; gradient: 0% to 40% EtOAc in heptane) to afford the title compound (112 mg, 88%) as a white solid. MS (ISP): 468.8 ([M+H]$^+$).

h) tert-butyl (11bR)-9-amino-1,3,4,6,7,11b-hexahydropyrazino[2,1-a]isoquinoline-2-carboxylate To a stirred solution of tert-butyl (11bR)-9-(benzhydrylideneamino)-1,3,4,6,7,11b-hexahydropyrazino[2,1-a]isoquinoline-2-carboxylate (435 mg, 0.93 mmol) in methanol (6 mL) were added sodium acetate (229 mg, 2.79 mmol) and hydroxylamine hydrochloride (142 mg, 2.05 mmol) and the reaction mixture was stirred at 50° C. overnight. The reaction mixture was then cooled to room temperature and partitioned between 1.0 M aqueous NaOH and EtOAc. The layers were separated and the organic layer was dried over Na$_2$SO$_4$ and concentrated in vacuo. The residue was purified by flash column chromatography (silica gel; gradient: 20% to 50% EtOAc+10% MeOH in heptane) to afford the title compound (252 mg, 89%) as an orange powder. MS (EI): 304.6 ([M+H]$^+$).

i) tert-butyl (11bR)-9-[[2-(trifluoromethyl)pyridine-4-carbonyl]amino]-1,3,4,6,7,11b-hexahydropyrazino[2,1-a]isoquinoline-2-carboxylate To a stirred solution of tert-butyl (11bR)-9-amino-1,3,4,6,7,11b-hexahydropyrazino[2,1-a]isoquinoline-2-carboxylate (20 mg, 0.066 mmol) in DMF (1 mL) were added sequentially N-methylmorpholine (27.1 0.198 mmol), HBTU (37.5 mg, 0.099 mmol) and 2-(trifluoromethyl)pyridine-4-carboxylic acid (16.4 mg, 0.086 mmol, CAS 131747-41-6). The resulting mixture was stirred at room temperature overnight before being partitioned between EtOAc and saturated aqueous NaHCO$_3$ (10 mL). The organic layers were washed with brine dried (Na$_2$SO$_4$) and concentrated in vacuo. The residue was purified by flash column chromatography (silica gel; gradient: 0% to 40% EtOAc in heptane) to afford the title compound (15 mg, 48%) as a white solid. MS (ISP): 477.7 ([M+H]$^+$).

j) N-[(11bR)-2,3,4,6,7,11b-hexahydro-1H-pyrazino[2,1-a]isoquinolin-9-yl]-2-(trifluoromethyl)pyridine-4-carboxamide hydrochloride To a stirred solution of tert-butyl (11bR)-9-[[2-(trifluoromethyl)pyridine-4-carbonyl]amino]-1,3,4,6,7,11b-hexahydropyrazino[2,1-a]isoquinoline-2-carboxylate (15 mg) in 1,4-dioxane (0.3 mL) was added a 4.0 m solution of HCl in dioxane (0.15 mL). The reaction mixture was stirred at 60° C. for 2 hours before being cooled to room temperature and stirred for further 12 hours. The resulting suspension was filtered through a sintered funnel. The collected hydrochloride salt was washed with further anhydrous diethyl ether then dried under high vacuum to afford the title compound (11.4 mg, 87%) as a white solid. MS (ISP): 376.1 ([M+H]$^+$).

Example 2

(11bR)-9-bromo-2,3,4,6,7,11b-hexahydro-1H-pyrazino[2,1-a]isoquinoline

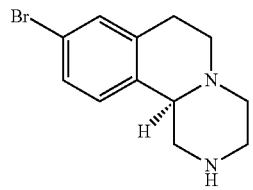 [SMILES: Brc1ccc2c(c1)CCN1CCNC[C@@H]21]

To a stirred solution of tert-butyl(−)-(11bR)-9-bromo-1,3,4,6,7,11b-hexahydropyrazino[2,1-a]isoquinoline-2-carboxylate (88 mg) in 1,4-dioxane (1 mL) was added a 4.0 m solution of HCl in 1,4-dioxane. The reaction mixture was stirred at 60° C. for 2 hours before being cooled to room temperature and stirred for further 12 hours. The resulting suspension was filtered through a sintered funnel. The collected hydrochloride salt was washed with further anhydrous diethyl ether then dried under high vacuum to afford the title compound (31 mg, 42%) as a white solid. MS (ISP): 270.5 ($[\{^{81}Br\}M+H]^+$), 268.5 ($[\{^{79}Br\}M+H]^+$).

Example 3

N-[(11bR)-2,3,4,6,7,11b-hexahydro-1H-pyrazino[2,1-a]isoquinolin-9-yl]-4-chloro-benzamide

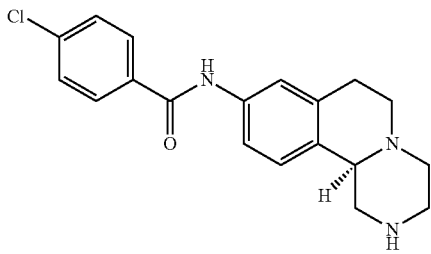 [SMILES: O=C(Nc1ccc2c(c1)CCN1CCNC[C@@H]21)c1ccc(Cl)cc1]

The title compound was obtained in analogy to Example 1 using 4-chlorobenzoic acid (CAS 74-11-3) in place of 2-(trifluoromethyl)isonicotinic acid in step (i). Off-white solid. MS (ISP): 344.6 ($[\{^{37}Cl\}M+H]^+$), 342.6 ($[\{^{35}Cl\}M+H]^+$).

Example 4

N-[(11bR)-2,3,4,6,7,11b-hexahydro-1H-pyrazino[2,1-a]isoquinolin-9-yl]-2-(trifluoromethyl)pyrimidine-5-carboxamide

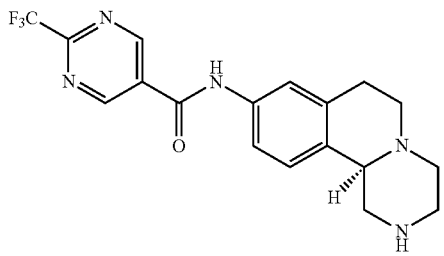 [SMILES: O=C(Nc1ccc2c(c1)CCN1CCNC[C@@H]21)c1cnc(C(F)(F)F)nc1]

The title compound was obtained in analogy to Example 1 using 2-(trifluoromethyl)pyrimidine-5-carboxylic acid (CAS 306960-74-7) in place of 2-(trifluoromethyl)isonicotinic acid in step (i). Off-white solid. MS (ISP): 376.3 ($[M+H]^+$).

Example 5

(11bR)—N-[2-(trifluoromethyl)pyrimidin-4-yl]-2,3,4,6,7,11b-hexahydro-1H-pyrazino[2,1-a]isoquinolin-9-amine

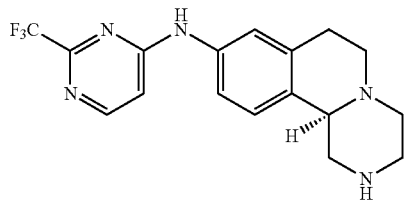 [SMILES: FC(F)(F)c1nccc(Nc2ccc3c(c2)CCN2CCNC[C@@H]32)n1]

a) tert-butyl (11bR)-9-[[5-(trifluoromethyl)pyrimidin-2-yl]amino]-1,3,4,6,7,11b-hexahydropyrazino[2,1-a]isoquinoline-2-carboxylate To a stirred solution of tert-butyl (11bR)-9-amino-1,3,4,6,7,11b-hexahydropyrazino[2,1-a]isoquinoline-2-carboxylate (25 mg, 0.082 mmol) in DMA (0.5 mL) and N,N-diisopropylethylamine (163 µl, 0.123 mmol) was added 4-chloro-2-(trifluoromethyl)pyrimidine (15 mg, 0.082 mmol) and the mixture was stirred at 100° C. overnight. The reaction mixture was then poured into water and extracted twice with EtOAc. The combined organic layers were washed with brine, dried (Na$_2$SO$_4$) and concentrated in vacuo. The residue was purified by flash column chromatography (silica gel; gradient: 0% to 100% EtOAc in heptane) to afford the title compound (10 mg, 27%) as a white solid. MS (ISP): 450.7 ($[M+H]^+$).

b) (11bR)—N-[2-(trifluoromethyl)pyrimidin-4-yl]-2,3,4,6,7,11b-hexahydro-1H-pyrazino[2,1-a]isoquinolin-9-amine To a stirred solution of tert-butyl (11bR)-9-[[5-(trifluoromethyl)pyrimidin-2-yl]amino]-1,3,4,6,7,11b-hexahydropyrazino[2,1-a]isoquinoline-2-carboxylate (10 mg) in 1,4-dioxane (0.5 mL) was added a 4.0 m solution of HCl in 1,4-dioxane. The reaction mixture was stirred at 60° C. for 2 hours before being cooled to room temperature and stirred for further 12 hours. All the volatiles were removed under vacuum and the residue was purified by preparative HPLC (mobile phase A: H$_2$O, B: CH$_3$CN with 0.05% Et$_3$N, C18 column) to afford the title compound (3.5 mg, 30%) as a white solid. MS (ISP): 350.5 ([M+H]+).

Example 6

(11bR)—N-[5-(trifluoromethyl)pyrimidin-2-yl]-2,3,4,6,7,11b-hexahydro-1H-pyrazino[2,1-a]isoquinolin-9-amine

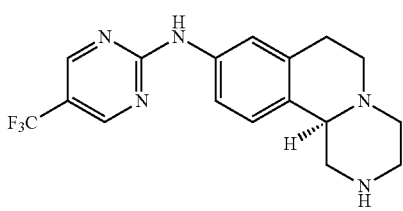 [SMILES: FC(F)(F)c1cnc(Nc2ccc3c(c2)CCN2CCNC[C@@H]32)nc1]

The title compound was obtained in analogy to Example 5 using 2-chloro-5-(trifluoromethyl)pyrimidine (CAS 69034-12-4) in place of 4-chloro-2-(trifluoromethyl)pyrimidine in step (a). Off-white solid. MS (ISP): 350.5 ([M+H]+).

Example 7

(11bR)—N-[5-(trifluoromethyl)pyrazin-2-yl]-2,3,4,6,7,11b-hexahydro-1H-pyrazino[2,1-a]isoquinolin-9-amine

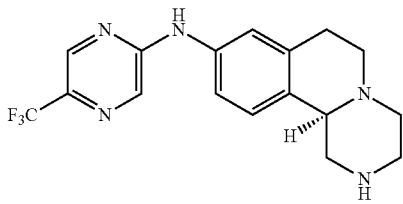 [SMILES: FC(F)(F)c1cnc(Nc2ccc3c(c2)CCN2CCNC[C@@H]32)cn1]

a) tert-butyl (11bR)-9-[[5-(trifluoromethyl)pyrazin-2-yl]amino]-1,3,4,6,7,11b-hexahydropyrazino[2,1-a]isoquinoline-2-carboxylate To a stirred solution of tert-butyl (11bR)-9-amino-1,3,4,6,7,11b-hexahydropyrazino[2,1-a]isoquinoline-2-carboxylate (25 mg, 0.082 mmol) in 1,4-dioxane (1.0 mL) were added 2-chloro-5-(trifluoromethyl)pyrazine (18 mg, 0.098 mmol), $Pd_2(dba)_3$ (7.55 mg, 8.24 µmol), xantphos (9.54 mg, 16.5 µmol, CAS 161265-03-8) and $Cs_2CO_3$ (40.3 mg, 124 µmol). The dark brown suspension was purged with a stream of argon for 10 min. The reaction mixture was heated to 100° C. and stirred for 17 h before being filtered on dicalite and concentrated in vacuo. The residue was poured into water and extracted twice with EtOAc. The organic layers were washed with brine, dried ($Na_2SO_4$) and concentrated in vacuo. The residue was purified by flash column chromatography (silica gel; gradient: 0% to 80% EtOAc in heptane) to afford the title compound (10 mg, 27%) as an orange oil. MS (ISP): 450.5 ([M+H]+).

b) (11bR)—N-[5-(trifluoromethyl)pyrazin-2-yl]-2,3,4,6,7,11b-hexahydro-1H-pyrazino[2,1-a]isoquinolin-9-amine hydrochloride To a stirred solution of tert-butyl (11bR)-9-[[5-(trifluoromethyl)pyrazin-2-yl]amino]-1,3,4,6,7,11b-hexahydropyrazino[2,1-a]isoquinoline-2-carboxylate (10 mg) in 1,4-dioxane (1.0 mL) was added a 4.0 M solution of HCl in 1,4-dioxane. The reaction mixture was stirred at 60° C. for 2 hours before being cooled to room temperature and stirred for further 12 hours. The resulting suspension was filtered through a sintered funnel. The collected hydrochloride salt was washed with further anhydrous diethyl ether then dried under high vacuum to afford the title compound (7 mg, 81%) as an orange solid. MS (ISP): 350.5 ([M+H]+).

Example 8

N-[(11bS)-2,3,4,6,7,11b-hexahydro-1H-pyrazino[2,1-a]isoquinolin-9-yl]-4-chloro-benzamide

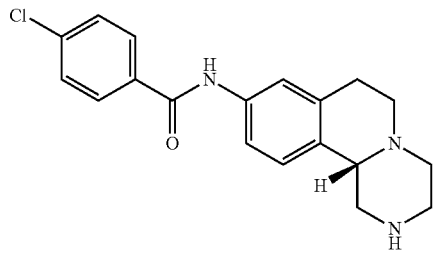 [SMILES: O=C(Nc1ccc2c(c1)CCN1CCNC[C@H]21)c1ccc(Cl)cc1]

The title compound was obtained in analogy to Example 1 using tert-butyl (11bS)-9-amino-1,3,4,6,7,11b-hexahydropyrazino[2,1-a]isoquinoline-2-carboxylate in place of tert-butyl (11bR)-9-amino-1,3,4,6,7,11b-hexahydropyrazino[2,1-a]isoquinoline-2-carboxylate and 4-chlorobenzoic acid (CAS 74-11-3) in place of 2-(trifluoromethyl)isonicotinic acid in step (i). Off-white solid. MS (ISP): 342.5 ([M+H]+).

Example 9

N-[(11bS)-2,3,4,6,7,11b-hexahydro-1H-pyrazino[2,1-a]isoquinolin-9-yl]-2-(trifluoromethyl)pyridine-4-carboxamide

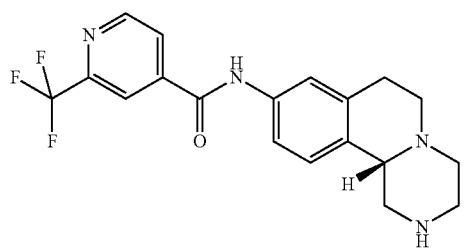 [SMILES: O=C(Nc1ccc2c(c1)CCN1CCNC[C@H]21)c1ccnc(C(F)(F)F)c1]

The title compound was obtained in analogy to Example 1 using tert-butyl (11bS)-9-amino-1,3,4,6,7,11b-hexahydropyrazino[2,1-a]isoquinoline-2-carboxylate in place of tert-butyl (11bR)-9-amino-1,3,4,6,7,11b-hexahydropyrazino[2,1-a]isoquinoline-2-carboxylate in step (i). Off-white solid. MS (ISP): 377.1 ([M+H]+).

Example 10

N-[(11bS)-2,3,4,6,7,11b-hexahydro-1H-pyrazino[2,1-a]isoquinolin-9-yl]-2-(trifluoromethyl)pyrimidine-5-carboxamide

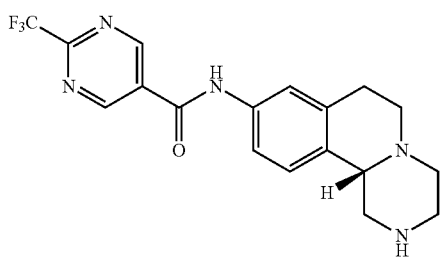 [SMILES: O=C(Nc1ccc2c(c1)CCN1CCNC[C@H]21)c1cnc(C(F)(F)F)nc1]

The title compound was obtained in analogy to Example 1 using tert-butyl (11bS)-9-amino-1,3,4,6,7,11b-hexahydro-pyrazino[2,1-a]isoquinoline-2-carboxylate in place of tert-butyl (11bR)-9-amino-1,3,4,6,7,11b-hexahydropyrazino[2,1-a]isoquinoline-2-carboxylate and 2-(trifluoromethyl)pyrimidine-5-carboxylic acid (CAS 306960-74-7) in place of 2-(trifluoromethyl)isonicotinic acid in step in step (i). Off-white solid. MS (ISP): 378.1 ([M+H]+).

Example 11

(11bS)—N-[2-(trifluoromethyl)pyrimidin-4-yl]-2,3,4,6,7,11b-hexahydro-1H-pyrazino[2,1-a]isoquinolin-9-amine

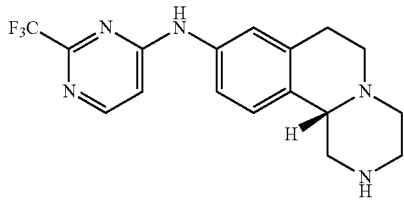 [SMILES: FC(F)(F)c1nccc(Nc2ccc3c(c2)CCN2CCNC[C@H]32)n1]

The title compound was obtained in analogy to Example 5 using tert-butyl (11bS)-9-amino-1,3,4,6,7,11b-hexahydro-pyrazino[2,1-a]isoquinoline-2-carboxylate in place of tert-butyl (11bR)-9-amino-1,3,4,6,7,11b-hexahydropyrazino[2,1-a]isoquinoline-2-carboxylate in step (a). Off-white solid. MS (ISP): 350.2 ([M+H]$^+$).

Example 12

(11bS)—N-[5-(trifluoromethyl)pyrazin-2-yl]-2,3,4,6,7,11b-hexahydro-1H-pyrazino[2,1-a]isoquinolin-9-amine

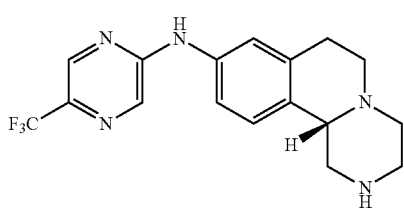 [SMILES: FC(F)(F)c1cnc(Nc2ccc3c(c2)CCN2CCNC[C@H]32)cn1]

The title compound was obtained in analogy to Example 7 using tert-butyl (11bS)-9-amino-1,3,4,6,7,11b-hexahydro-pyrazino[2,1-a]isoquinoline-2-carboxylate in place of tert-butyl (11bR)-9-amino-1,3,4,6,7,11b-hexahydropyrazino[2,1-a]isoquinoline-2-carboxylate in step (a). Orange powder. MS (ISP): 350.2 ([M+H]$^+$).

Example 13

(R)—N-(5-(2,2,2-trifluoroethoxy)pyrimidin-2-yl)-2,3,4,6,7,11b-hexahydro-1H-pyrazino[2,1-a]isoquinolin-9-amine

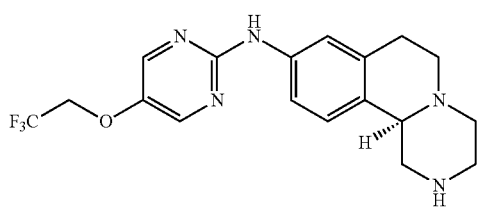 [SMILES: FC(F)(F)COc1cnc(Nc2ccc3c(c2)CCN2CCNC[C@@H]32)nc1]

The title compound was obtained in analogy to Example 7 using 2-chloro-5-(2,2,2-trifluoroethoxy)pyrimidine in place of 2-chloro-5-(trifluoromethyl)pyrazine in step (a). Light yellow solid. MS (ISP): 380.2 ([M+H]$^+$).

Example 14

(11bR)—N-(5-cyclopropylpyrimidin-2-yl)-2,3,4,6,7,11b-hexahydro-1H-pyrazino[2,1-a]isoquinolin-9-amine

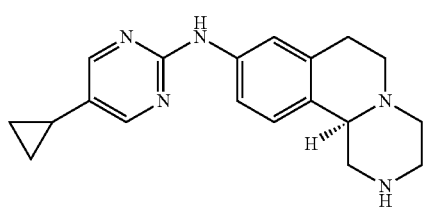 [SMILES: c1cc2c(cc1Nc1ncc(C3CC3)cn1)CCN1CCNC[C@@H]21]

The title compound was obtained in analogy to Example 7 using 2-chloro-5-cyclopropylpyrimidine (CAS 166740-44-9) in place of 2-chloro-5-(trifluoromethyl)pyrazine in step (a). Orange solid. MS (ISP): MS (ISP): 322.2 ([M+H]$^+$).

Example 15

(11bR)-2,3,4,6,7,11b-hexahydro-1H-pyrazino[2,1-a]isoquinoline

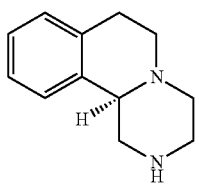 [SMILES: c1ccc2c(c1)CCN1CCNC[C@@H]21]

To a stirred solution of tert-butyl (11bR)-9-bromo-1,3,4,6,7,11b-hexahydropyrazino[2,1-a]isoquinoline-2-carboxylate (101 mg, 0.275 mmol) in MeOH (4 mL) was added 10 wt. % Pd/C (29.3 mg, 0.027 mmol) and the resulting black suspension was purged by evacuation and then back filled with a stream of hydrogen (balloon) for three times. The mixture was stirred for 16 hours at room temperature under a hydrogen atmosphere and then filtered through a pad of dicalite. The filter cake was rinsed with EtOAc and the filtrate concentrate in vacuum. The residue was dissolved in CH$_2$Cl$_2$ (4.0 mL) then TFA (2.0 mL) was added. The resulting yellow solution was stirred at room temperature for 2 hours before all volatiles were removed under vacuum to afford the title compound (31.9 mg, 38%) as a light yellow oil.

Example 16

N-[(11bR)-10-fluoro-2,3,4,6,7,11b-hexahydro-1H-pyrazino[2,1-a]isoquinolin-9-yl]-2-(trifluoromethyl)pyridine-4-carboxamide

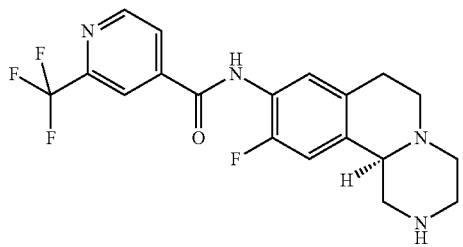 [SMILES: O=C(Nc1cc2c(cc1F)[C@@H]1CNCCN1CC2)c1ccnc(C(F)(F)F)c1]

a) 2-(3-bromo-4-fluorophenyl)ethanamine

To a stirred solution of 2-(3-bromo-4-fluoro-phenyl)acetonitrile (5.0 g, 22.9 mmol, CAS 501420-63-9) in THF (50 mL) was added borane-tetrahydrofuran complex 1.0 M in THF (45.8 mL, 45.8 mmol) at 0° C. The mixture was stirred at room temperature for 1 hour then heated to reflux overnight. The reaction mixture was then re-cooled to 0° C. and MeOH (25 mL) was added. The mixture was heated to reflux for 90 min. The solvent was removed under vacuum and the residue was partitioned between EtOAc and aqueous 1.0 M HCl. The aqueous phase was made basic with aqueous 1.0 M NaOH then extracted with EtOAc. Organic layers were washed with saturated brine, dried (Na$_2$SO$_4$) and concentrated in vacuo to afford the title compound (2.79 g, 56%) as viscous yellow oil which was used in the next step without further purification.

b) N-(3-bromo-4-fluorophenethyl)-2-chloroacetamide

To a suspension of 2-(3-bromo-4-fluorophenyl)ethanamine (2.79 g, 12.8 mmol) and NaHCO$_3$ (4.28 g, 50.9 mmol) in dichloromethane (15 mL) was added dropwise chloroacetyl chloride (1.23 mL, 15.4 mmol) at 0° C. during 30 min. The reaction mixture was allowed to warm to room temperature overnight, before being quenched by slow addition of water at 0° C. The organic layer was separated, and washed successively with 10% aqueous HCl solution and brine, dried (Na$_2$SO$_4$), filtered and concentrated in vacuo to afford the title compound (3.8 g) as a viscous yellow oil which was used in the next step without further purification.

c) N-(3-bromo-4-fluorophenethyl)-2-(2,2-dimethoxyethylamino)acetamide

To a solution of N-(3-bromo-4-fluorophenethyl)-2-chloroacetamide (3.8 g, 12.9 mmol) in toluene (20 mL) was added aminoacetaldehyde dimethyl acetal (2.79 mL, 25.8 mmol, CAS 22483-09-6) and the mixture was heated to reflux for 2 hours. After cooling to room temperature, the solvent was evaporated and the residue partitioned between EtOAc and water. The phases were separated and the organic layer was dried over Na$_2$SO$_4$ and concentrated in vacuo to afford the title compound (3.9 g) as an orange oil which was used in the next step without further purification.

d) 9-bromo-10-fluoro-1,2,3,6,7,11b-hexahydropyrazino[2,1-a]isoquinolin-4-one

To a solution of N-(3-bromo-4-fluorophenethyl)-2-(2,2-dimethoxyethylamino)acetamide (3.9 g, 10.7 mmol) in CH$_2$Cl$_2$ (8 mL) was added dropwise sulfuric acid (3.72 mL, 69.8 mmol) at 0-5° C. The reaction mixture was allowed to warm up to room temperature for 1 hour before being poured into ice-water. The pH was adjusted to 12 by addition of aqueous NaOH (20 wt. %) while cooling. The water phase was extracted with CH$_2$Cl$_2$ twice. The combined organic extracts were washed with brine, dried (Na$_2$SO$_4$), filtered and concentrated in vacuo. The residue was purified by flash chromatography (silica gel, gradient 5% to 10% MeOH in CH$_2$Cl$_2$) to afford the title compound (650 mg, 20% yield) as an orange foam. MS (ISP): 301.0 ([{$^{81}$Br}M+H]$^+$), 299.0 ([{$^{79}$Br}M+H]$^+$)

e) tert-butyl 9-bromo-10-fluoro-4-oxo-3,4,6,7-tetrahydro-1H-pyrazino[2,1-a]isoquinoline-2(11bH)-carboxylate To a stirred solution of 9-bromo-10-fluoro-1,2,3,6,7,11b-hexahydropyrazino[2,1-a]isoquinolin-4-one (650 mg, 2.17 mmol) and Et$_3$N (1.06 mL, 7.61 mmol) in CH$_2$Cl$_2$ (14 mL) was added Boc$_2$O (569 mg, 2.61 mmol) and the mixture was stirred at room temperature for 16 hours. The reaction mixture was partitioned between aqueous citric (10 wt. %) acid and CH$_2$Cl$_2$. The layers were separated and the organic phase was washed with saturated aqueous NaHCO$_3$, dried (Na$_2$SO$_4$) and concentrated in vacuo. The residue was purified by flash column chromatography (silica gel; gradient: 0% to 40% EtOAc in heptane) to afford the title compound (840 mg, 94%) as viscous yellow oil.

f) tert-butyl (11bR)-9-bromo-10-fluoro-4-oxo-3,6,7,11b-tetrahydro-1H-pyrazino[2,1-a]isoquinoline-2-carboxylate & tert-butyl (11bS)-9-bromo-10-fluoro-4-oxo-3,6,7,11b-tetrahydro-1H-pyrazino[2,1-a]isoquinoline-2-carboxylate The enantiomers of (RS)-tert-butyl 9-bromo-10-fluoro-4-oxo-3,4,6,7-tetrahydro-1H-pyrazino[2,1-a]isoquinoline-2(11bH)-carboxylate (840 mg) were separated using chiral HPLC (column: Reprosil chiral-NR, 250×50 mm; eluent: 30% ethanol/heptane; pressure: 18 bar; flow rate: 35 mL/min) affording:
(+)-tert-butyl (11bS)-9-bromo-10-fluoro-4-oxo-3,6,7,11b-tetrahydro-1H-pyrazino[2,1-a]isoquinoline-2-carboxylate (363 mg, light orange solid), retention time=33 min (−)-tert-butyl (11bR)-9-bromo-10-fluoro-4-oxo-3,6,7,11b-tetrahydro-1H-pyrazino[2,1-a]isoquinoline-2-carboxylate (329 mg, light orange solid), retention time=42 min g) tert-butyl (11bR)-9-bromo-10-fluoro-1,3,4,6,7,11b-hexahydropyrazino[2,1-a]isoquinoline-2-carboxylate To a stirred solution of tert-butyl (11bR)-9-bromo-10-fluoro-4-oxo-3,6,7,11b-tetrahydro-1H-pyrazino[2,1-a]isoquinoline-2-carboxylate (329 mg, 0.824 mmol) in THF (13 mL) was added borane-tetrahydrofuran complex 1.0 M in THF (4.94 mL, 4.94 mmol) and the mixture was stirred at room temperature for 16 hours. The reaction mixture was then poured into saturated aqueous NaHCO$_3$ and extracted twice with EtOAc. The combined organic extracts were washed with saturated brine, dried (Na$_2$SO$_4$) and concentrated in vacuo. The residue was purified by flash column chromatography (silica gel; gradient: 0% to 30% EtOAc in heptane) to afford the title compound (240 mg, 75%) as a white powder. MS (ISP): 388.3 ([{$^{81}$Br}M+H]$^+$), 386.3 ([{$^{79}$Br}M+H]$^+$).

h) tert-butyl (11bR)-9-(benzhydrylideneamino)-10-fluoro-1,3,4,6,7,11b-hexahydropyrazino[2,1-a]isoquinoline-2-carboxylate A screw-cap vial was charged with tert-butyl (11bR)-9-bromo-10-fluoro-1,3,4,6,7,11b-hexahydropyrazino[2,1-a]isoquinoline-2-carboxylate (140 mg, 0.363 mmol), benzophenone imine (132 mg, 0.727 mmol, CAS 1013-88-3), (rac)-2,2'-bis(diphenylphosphino)-1,1'-binaphthyl (22.6 mg, 0.036 mmol), tris(dibenzylideneacetone)dipalladium(0) (10 mg, 0.010 mmol) and sodium tert-butoxide (56 mg, 0.581 mmol). The vial was then degassed by alternative evacuation and back filling with argon. Toluene (2.5 mL) was added and the resulting mixture was flushed with a stream of argon for 10 min. The reaction mixture was heated to 90° C. in an oil bath for 3 hours then filtered directly through a plug of dicalite. The filter cake was rinsed with EtOAc and the filtrate was washed with brine, dried (Na$_2$SO$_4$) and concentrated in vacuo. The residue was purified by flash column chromatography (silica gel; gradient: 0% to 70% EtOAc in heptane) to afford the title compound (66 mg, 37%) as a yellow waxy solid. MS (ISP): 486.4 ([M+H]$^+$).

i) tert-butyl (11bR)-9-amino-10-fluoro-1,3,4,6,7,11b-hexahydropyrazino[2,1-a]isoquinoline-2-carboxylate To a stirred solution of tert-butyl (11bR)-9-(benzhydrylideneamino)-10-fluoro-1,3,4,6,7,11b-hexahydropyrazino[2,1-a]isoquinoline-2-carboxylate (66 mg, 0.136 mmol) in methanol (2.0 mL) was added sodium acetate (33.4 mg, 0.408 mmol), hydroxylamine hydrochloride (21 mg, 0.300 mmol) and the reaction mixture was stirred at 50° C. overnight. The reaction mixture was then cooled to room temperature and partitioned between 1.0 m aqueous NaOH and EtOAc. The layers were separated and the organic layer was dried over Na$_2$SO$_4$ and concentrated in vacuo. The residue was purified by flash column chromatography (silica gel; gradient: 20% to 50% EtOAc+10% MeOH in heptane) to afford the title compound (40 mg, 91%) as colorless foam. MS (EI): 322.3 ([M+H]$^+$).

j) tert-butyl (11bR)-10-fluoro-9-[[2-(trifluoromethyl)pyridine-4-carbonyl]amino]-1,3,4,6,7,11b-hexahydropyrazino[2,1-a]isoquinoline-2-carboxylate To a stirred solution of tert-butyl (11bR)-9-amino-10-fluoro-1,3,4,6,7,11b-hexahydropyrazino[2,1-a]isoquinoline-2-carboxylate (20 mg, 0.062 mmol) in DMF (1 mL) were added sequentially N-methylmorpholine (20.5 µl, 0.186 mmol), HBTU (35.4 mg, 0.093 mmol) and 2-(trifluoromethyl)pyridine-4-carboxylic acid (15.5 mg, 0.081 mmol, CAS 131747-41-6). The resulting mixture was stirred at room temperature overnight before being partitioned between EtOAc and saturated aqueous NaHCO$_3$ (10 mL). The organic layers were washed with brine dried (Na$_2$SO$_4$) and concentrated in vacuo. The residue was purified by flash column chromatography (silica gel; gradient: 0% to 70% EtOAc in heptane) to afford the title compound (18 mg, 58%) as a yellow oil. MS (ISP): 495.3 ([M+H]$^+$).

k) N-[(11bR)-10-fluoro-2,3,4,6,7,11b-hexahydro-1H-pyrazino[2,1-a]isoquinolin-9-yl]-2-(trifluoromethyl)pyridine-4-carboxamide hydrochloride To a stirred solution of tert-butyl (11bR)-10-fluoro-9-[[2-(trifluoromethyl)pyridine-4-carbonyl]amino]-1,3,4,6,7,11b-hexahydropyrazino[2,1-a]isoquinoline-2-carboxylate (18 mg, 0.036 mmol) in 1,4-dioxane (0.5 mL) was added a 4.0 m solution of HCl in dioxane (0.25 mL). The reaction mixture was stirred at 60° C. for 2 hours before being cooled to room temperature and stirred for further 12 hours. The resulting suspension was filtered through a sintered funnel. The collected hydrochloride salt was washed with further anhydrous diethyl ether then dried under high vacuum to afford the title compound (15 mg, 95%) as a light yellow solid. MS (ISP): 395.3 ([M+H]$^+$).

Example 17

(11bR)-10-fluoro-N-[5-(trifluoromethyl)pyrimidin-2-yl]-2,3,4,6,7,11b-hexahydro-1H-pyrazino[2,1-a]isoquinolin-9-amine

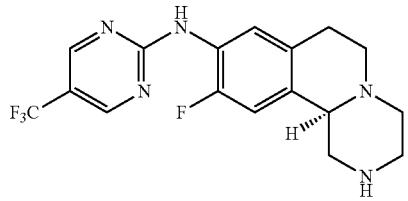 [SMILES: Fc1cc2c(cc1Nc1ncc(C(F)(F)F)cn1)CCN1CCNC[C@@H]21]

a) tert-butyl (11bR)-10-fluoro-9-[[5-(trifluoromethyl)pyrimidin-2-yl]amino]-1,3,4,6,7,11b-hexahydropyrazino[2,1-a]isoquinoline-2-carboxylate To a stirred solution of tert-butyl (11bR)-9-amino-10-fluoro-1,3,4,6,7,11b-hexahydropyrazino[2,1-a]isoquinoline-2-carboxylate (20 mg, 0.062 mmol) in DMA (0.5 mL) and N,N-diisopropylethylamine (123 µl, 0.093 mmol) was added 2-chloro-5-(trifluoromethyl)pyrimidine (11.4 mg, 0.062 mmol) and the mixture was stirred at 100° C. overnight. The reaction mixture was then poured into water and extracted twice with EtOAc. The combined organic layers were washed with brine, dried (Na$_2$SO$_4$) and concentrated in vacuo. The residue was purified by preparative HPLC (mobile phase A: H$_2$O, B: CH$_3$CN with 0.05% Et$_3$N, C18 column) to afford the title compound (10 mg, 34%) as a white solid. MS (ISP): 468.3 ([M+H]$^+$).

b) (11bR)-10-fluoro-N-[5-(trifluoromethyl)pyrimidin-2-yl]-2,3,4,6,7,11b-hexahydro-1H-pyrazino[2,1-a]isoquinolin-9-amine hydrochloride To a stirred solution of tert-butyl (11bR)-10-fluoro-9-[[5-(trifluoromethyl)pyrimidin-2-yl]amino]-1,3,4,6,7,11b-hexahydropyrazino[2,1-a]isoquinoline-2-carboxylate (10 mg) in 1,4-dioxane (0.5 mL) was added a 4.0 m solution of HCl in dioxane (0.25 mL). The reaction mixture was stirred at 60° C. for 2 hours before being cooled to room temperature and stirred for further 6 hours. The resulting suspension was filtered through a sintered funnel. The collected hydrochloride salt was washed with further anhydrous diethyl ether then dried under high vacuum to afford the title compound (3 mg, 37%) as a light yellow solid. MS (ISP): 368.1 ([M+H]$^+$).

Example 18

(11bR)—N-[6-methoxy-2-(trifluoromethyl)pyrimidin-4-yl]-2,3,4,6,7,11b-hexahydro-1H-pyrazino[2,1-a]isoquinolin-9-amine

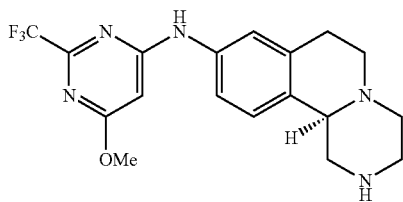 [SMILES: COc1cc(Nc2ccc3c(c2)CCN2CCNC[C@@H]32)nc(C(F)(F)F)n1]

a) tert-butyl (11bR)-9-[[6-chloro-2-(trifluoromethyl)pyrimidin-4-yl]amino]-1,3,4,6,7,11b-hexahydropyrazino[2,1-a]isoquinoline-2-carboxylate To a stirred solution of tert-butyl (11bR)-9-amino-1,3,4,6,7,11b-hexahydropyrazino[2,1-a]isoquinoline-2-carboxylate (95 mg, 0.313 mmol) in DMA (1.0 mL) and N,N-diisopropylethylamine (57 µl, 0.043 mmol) was added 4,6-dichloro-2-(trifluoromethyl)pyrimidine (39.3 mg, 0.470 mmol) and the mixture was stirred at 80° C. for 2 hours. The reaction mixture was then poured into water and extracted twice with EtOAc. The combined organic layers were washed with brine, dried (Na$_2$SO$_4$) and concentrated in vacuo. The residue was purified by flash column chromatography (silica gel; gradient: 0% to 40% EtOAc in heptane) to afford the title compound (105 mg, 69%) as a yellow solid. MS (ISP): 486.2 ([{$^{37}$Cl}M+H]$^+$), 484.2 ([{$^{35}$Cl}M+H]$^+$).

b) tert-butyl (11bR)-9-[[6-methoxy-2-(trifluoromethyl)pyrimidin-4-yl]amino]-1,3,4,6,7,11b-hexahydropyrazino[2,1-a]isoquinoline-2-carboxylate To a stirred solution of tert-butyl (11bR)-9-[[6-chloro-2-(trifluoromethyl)pyrimidin-4-yl]amino]-1,3,4,6,7,11b-hexahydropyrazino[2,1-a]isoquinoline-2-carboxylate (30 mg, 0.062 mmol) in methanol (0.5 mL) was added a solution of sodium methoxide (310 ul, 0.062 mmol, 25 wt. %) in methanol and the reaction mixture was stirred at 65° C. for 48 hours. The reaction mixture was poured onto water and extracted twice with EtOAc. The layers were separated and the organic phase was washed with brine, dried (Na$_2$SO$_4$) and concentrated in vacuo. The residue was purified by flash column chromatography (silica gel; gradient: 0% to 40% EtOAc in heptane) to afford the title compound (14.2 mg, 48%) as colorless viscous oil. MS (ISP): 480.3 ([M+H]+).

c) (11bR)—N-[6-methoxy-2-(trifluoromethyl)pyrimidin-4-yl]-2,3,4,6,7,11b-hexahydro-1H-pyrazino[2,1-a]isoquinolin-9-amine hydrochloride To a stirred solution of tert-butyl (11bR)-9-[[6-methoxy-2-(trifluoromethyl)pyrimidin-4-yl]amino]-1,3,4,6,7,11b-hexahydropyrazino[2,1-a]isoquinoline-2-carboxylate (14.2 mg) in 1,4-dioxane (0.5 mL) was added a 4.0 m solution of HCl in dioxane (0.25 mL). The reaction mixture was stirred at 60° C. for 2 hours before being cooled to room temperature and stirred for further 6 hours. The resulting suspension was filtered through a sintered funnel. The collected hydrochloride salt was washed with further anhydrous diethyl ether then dried under high vacuum to afford the title compound (10 mg, 82%) as an off-white solid. MS (ISP): 378.3 ([M−H]$^−$).

Example 19

N4-[(11bR)-2,3,4,6,7,11b-hexahydro-1H-pyrazino[2,1-a]isoquinolin-9-yl]-N6,N6-dimethyl-2-(trifluoromethyl)pyrimidine-4,6-diamine

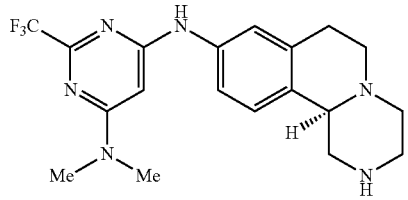 [SMILES: CN(C)c1cc(Nc2ccc3c(c2)CCN2CCNC[C@@H]32)nc(C(F)(F)F)n1]

a) tert-butyl (11bR)-9-[[6-(dimethylamino)-2-(trifluoromethyl)pyrimidin-4-yl]amino]-1,3,4,6,7,11b-hexahydropyrazino[2,1-a]isoquinoline-2-carboxylate To a stirred solution of tert-butyl (11bR)-9-[[6-chloro-2-(trifluoromethyl)pyrimidin-4-yl]amino]-1,3,4,6,7,11b-hexahydropyrazino[2,1-a]isoquinoline-2-carboxylate (30 mg, 0.062 mmol) in DMA (0.25 mL) was added dimethyl amine (62 µl, 0.124 mmol) and the reaction mixture was stirred at 100° C. for 3 hours. The reaction mixture was poured onto water and extracted twice with EtOAc. The layers were separated and the organic phase was washed with brine, dried (Na$_2$SO$_4$) and concentrated in vacuo. The residue was purified by flash column chromatography (silica gel; gradient: 0% to 50% EtOAc in heptane) to afford the title compound (17.4 mg, 57%) as colorless viscous oil. MS (ISP): 493.4 ([M+H]$^+$).

b) N4-[(11bR)-2,3,4,6,7,11b-hexahydro-1H-pyrazino[2,1-a]isoquinolin-9-yl]-N6,N6-dimethyl-2-(trifluoromethyl)pyrimidine-4,6-diamine hydrochloride To a stirred solution of tert-butyl (11bR)-9-[[6-(dimethylamino)-2-(trifluoromethyl)pyrimidin-4-yl]amino]-1,3,4,6,7,11b-hexahydropyrazino[2,1-a]isoquinoline-2-carboxylate (17.4 mg) in 1,4-dioxane (0.5 mL) was added a 4.0 m solution of HCl in dioxane (0.25 mL). The reaction mixture was stirred at 60° C. for 2 hours before being cooled to room temperature and stirred for further 6 hours. The resulting suspension was filtered through a sintered funnel. The collected hydrochloride salt was washed with further anhydrous diethyl ether then dried under high vacuum to afford the title compound (8 mg, 53%) as an orange solid. MS (ISP): 393.3 ([M+H]$^+$).

Example 20

(11bR)—N-[6-methyl-2-(trifluoromethyl)pyrimidin-4-yl]-2,3,4,6,7,11b-hexahydro-1H-pyrazino[2,1-a]isoquinolin-9-amine

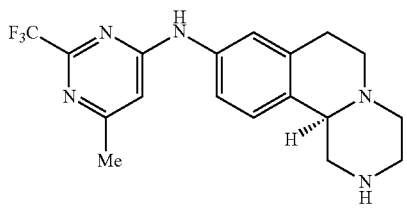 [SMILES: Cc1cc(Nc2ccc3c(c2)CCN2CCNC[C@@H]32)nc(C(F)(F)F)n1]

a) tert-butyl (11bR)-9-[[6-methyl-2-(trifluoromethyl)pyrimidin-4-yl]amino]-1,3,4,6,7,11b-hexahydropyrazino[2,1-a]isoquinoline-2-carboxylate A screw-cap vial was charged with tert-butyl (11bR)-9-[[6-chloro-2-(trifluoromethyl)pyrimidin-4-yl]amino]-1,3,4,6,7,11b-hexahydropyrazino[2,1-a]isoquinoline-2-carboxylate (30 mg, 0.062 mmol), Cs$_2$CO$_3$ (80.8 mg, 0.248 mmol), trimethylboroxine (17.3 μl, 124 μmol, CAS 823-96-1), and bis(tricyclohexylphosphine)palladium(0) (4.14 mg, 6.2 μmol, CAS 33309-88-5). The vial was then degassed by alternative evacuation and back filling with argon. 1,4-Dioxane (2.0 mL) was added and the resulting mixture was flushed with a stream of argon for 10 min. The reaction mixture was heated to 80° C. in an oil bath for 4 hours then filtered directly through a plug of dicalite. The filter cake was rinsed with EtOAc and the filtrate was washed with brine, dried (Na$_2$SO$_4$) and concentrated in vacuo. The residue was purified by flash column chromatography (silica gel; gradient: 0% to 70% EtOAc in heptane) to afford the title compound (20.4 mg, 71%) as a light yellow solid.

b) (11bR)—N-[6-methyl-2-(trifluoromethyl)pyrimidin-4-yl]-2,3,4,6,7,11b-hexahydro-1H-pyrazino[2,1-a]isoquinolin-9-amine hydrochloride To a stirred solution of tert-butyl (11bR)-9-[[6-methyl-2-(trifluoromethyl)pyrimidin-4-yl]amino]-1,3,4,6,7,11b-hexahydropyrazino[2,1-a]isoquinoline-2-carboxylate (20.4 mg) in 1,4-dioxane (0.5 mL) was added a 4.0 m solution of HCl in dioxane (0.25 mL). The reaction mixture was stirred at 60° C. for 2 hours before being cooled to room temperature and stirred for further 6 hours. The resulting suspension was filtered through a sintered funnel. The collected hydrochloride salt was washed with further anhydrous diethyl ether then dried under high vacuum to afford the title compound (9 mg, 51%) as a white solid. MS (ISP): 364.2 ([M+H]$^+$).

Example 21

(11bR)—N-[6-chloro-2-(trifluoromethyl)pyrimidin-4-yl]-2,3,4,6,7,11b-hexahydro-1H-pyrazino[2,1-a]isoquinolin-9-amine

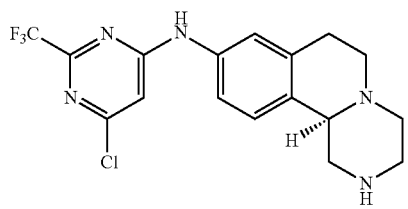 [SMILES: FC(F)(F)c1nc(Cl)cc(Nc2ccc3c(c2)CCN2CCNC[C@@H]32)n1]

To a stirred solution of with tert-butyl (11bR)-9-[[6-chloro-2-(trifluoromethyl)pyrimidin-4-yl]amino]-1,3,4,6,7,11b-hexahydropyrazino[2,1-a]isoquinoline-2-carboxylate (20 mg, 0.062 mmol) in 1,4-dioxane (0.5 mL) was added a 4.0 m solution of HCl in dioxane (0.25 mL). The reaction mixture was stirred at 60° C. for 2 hours before being cooled to room temperature and stirred for further 6 hours. The resulting suspension was filtered through a sintered funnel. The collected hydrochloride salt was washed with further anhydrous diethyl ether then dried under high vacuum to afford the title compound (5 mg, 30%) as a white solid. MS (ISP): 386.2 ([{$^{37}$Cl}M+H]$^+$), 384.2 ([{$^{35}$Cl}M+H]$^+$).

Example 22

(11bR)—N-pyrimidin-2-yl-2,3,4,6,7,11b-hexahydro-1H-pyrazino[2,1-a]isoquinolin-9-amine

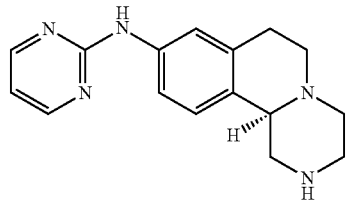 [SMILES: c1cnc(Nc2ccc3c(c2)CCN2CCNC[C@@H]32)nc1]

The title compound was obtained in analogy to Example 7 using 2-chloropyrimidine (CAS 1722-12-9) in place of 2-chloro-5-(trifluoromethyl)pyrazine in step (a). Off-white solid. MS (ISP): 282.2 ([M+H]$^+$).

Example 23

(11bR)—N-(2,6-dimethylpyrimidin-4-yl)-2,3,4,6,7,11b-hexahydro-1H-pyrazino[2,1-a]isoquinolin-9-amine

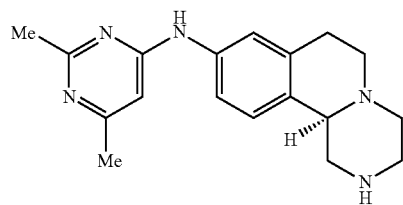 [SMILES: Cc1cc(Nc2ccc3c(c2)CCN2CCNC[C@@H]32)nc(C)n1]

The title compound was obtained in analogy to Example 7 using 4-chloro-2,6-dimethylpyrimidine (CAS 32314-39-9) in place of 2-chloro-5-(trifluoromethyl)pyrazine in step (a). Off-white solid. MS (ISP): 310.2 ([M+H]⁺).

Example 24

(11bR)—N-[4-(trifluoromethyl)pyrimidin-2-yl]-2,3,4,6,7,11b-hexahydro-1H-pyrazino[2,1-a]isoquinolin-9-amine

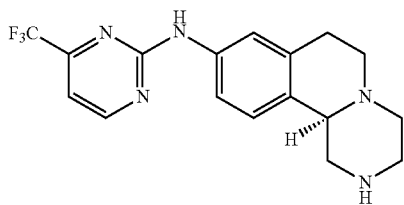 [SMILES: FC(F)(F)c1ccnc(Nc2ccc3c(c2)CCN2CCNC[C@@H]32)n1]

The title compound was obtained in analogy to Example 7 using 2-chloro-4-(trifluoromethyl)pyrimidine (CAS 33034-67-2) in place of 2-chloro-5-(trifluoromethyl)pyrazine in step (a). Off-white solid. MS (ISP): 350.2 ([M+H]⁺).

Example 25

(11bR)—N-(5-ethylpyrimidin-2-yl)-2,3,4,6,7,11b-hexahydro-1H-pyrazino[2,1-a]isoquinolin-9-amine

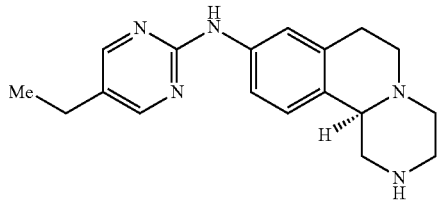 [SMILES: CCc1cnc(Nc2ccc3c(c2)CCN2CCNC[C@@H]32)nc1]

The title compound was obtained in analogy to Example 7 using 2-chloro-5-ethylpyrimidine (CAS 111196-81-7) in place of 2-chloro-5-(trifluoromethyl)pyrazine in step (a). Light brown solid. MS (ISP): 310.2 ([M+H]⁺).

Example 26

(R)—N-(6-methyl-2-(2,2,2-trifluoroethoxy)pyrimidin-4-yl)-2,3,4,6,7,11b-hexahydro-1H-pyrazino[2,1-a]isoquinolin-9-amine

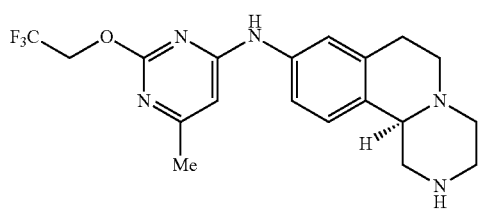 [SMILES: Cc1cc(Nc2ccc3c(c2)CCN2CCNC[C@@H]32)nc(OCC(F)(F)F)n1]

a) 6-methyl-2-(2,2,2-trifluoroethoxy)pyrimidin-4-amine

To a stirred solution of 2-chloro-6-methylpyrimidin-4-amine (718 mg, 5.00 mmol, CAS 14394-60-6) in THF (10 mL) was added NaH (240 mg, 60% in mineral oil, 6.0 mmol) at room temperature. After 30 minutes, 2,2,2-trifluoroethanol (500 mg, 5.00 mmol, CAS 75-89-8) was added and the mixture was heated to 75° C. for 16 hours before being partitioned between water and EtOAc. The layers were separated and the organic phase was washed with brine, dried (Na₂SO₄) and concentrated in vacuo to afford the title compound as white solid which was used in the next step without further purification.

b) tert-butyl (11bR)-9-[[6-methyl-2-(2,2,2-trifluoroethoxy)pyrimidin-4-yl]amino]-1,3,4,6,7,11b-hexahydropyrazino[2,1-a]isoquinoline-2-carboxylate A screw-cap vial was charged with tert-butyl (11bR)-9-bromo-1,3,4,6,7,11b-hexahydropyrazino[2,1-a]isoquinoline-2-carboxylate (60 mg, 0.163 mmol), 6-methyl-2-(2,2,2-trifluoroethoxy)pyrimidin-4-amine (40.6 mg, 0.196 mmol), tris(dibenzylideneacetone)dipalladium (15 mg, 0.016 mmol), 2-di-tert-butylphosphino-2',4',6'-triisopropylbiphenyl (14 mg, 0.037 mmol, CAS 564483-19-8) and sodium tert-butoxide (17.3 mg, 0.180 mmol). The vial was then degassed by alternative evacuation and back filling with argon. 1,4-dioxane (1.0 mL) was added and the resulting mixture was flushed with a stream of argon for 10 min. The reaction mixture was heated to 100° C. in an oil bath for 16 hours then filtered directly through a plug of dicalite. The filter cake was rinsed with EtOAc and the filtrate was washed with brine, dried (Na₂SO₄) and concentrated in vacuo. The residue was purified by flash column chromatography (silica gel; gradient: 0% to 80% EtOAc in heptane) to afford the title compound (20 mg, 25%) as an orange viscous oil. MS (ISP): 492.4 ([M−H]⁻).

c) (R)—N-(6-methyl-2-(2,2,2-trifluoroethoxy)pyrimidin-4-yl)-2,3,4,6,7,11b-hexahydro-1H-pyrazino[2,1-a]isoquinolin-9-amine To a stirred solution of tert-butyl (11bR)-9-[[6-methyl-2-(2,2,2-trifluoroethoxy)pyrimidin-4-yl]amino]-1,3,4,6,7,11b-hexahydropyrazino[2,1-a]isoquinoline-2-carboxylate (20 mg) in 1,4-dioxane (0.5 mL) was added a 4.0 m solution of HCl in 1,4-dioxane (0.25 mL). The reaction mixture was stirred at 60° C. for 2 hours before being cooled to room temperature and stirred for further 6 hours. All the volatiles were removed under vacuum and the residue was purified by preparative HPLC (mobile phase A: H₂O, B: CH₃CN with 0.05% Et₃N, C18 column) to afford the title compound (6 mg, 37%) as a white solid. MS (ISP): 392.3, ([M−H]⁻).

Example 27

(11bR)-9-ethyl-2,3,4,6,7,11b-hexahydro-1H-pyrazino[2,1-a]isoquinoline

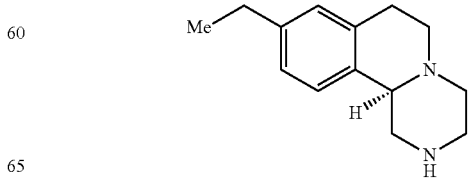

a) tert-butyl (11bR)-9-ethyl-1,3,4,6,7,11b-hexahydropyrazino[2,1-a]isoquinoline-2-carboxylate A 5 mL microwave reactor was charged with tert-butyl (11bR)-9-bromo-1,3,4,6,7,11b-hexahydropyrazino[2,1-a]isoquinoline-2-carboxylate (30 mg, 0.0817 mmol), ethylboronic acid (7.83 mg, 0.106 mmol, CAS 4433-63-0), dipotassium phosphate (35.6 mg, 0.204 mmol) and Pd(OAc)$_2$ (0.91 mg, 4.1 µmol). The vial was then degassed by alternative evacuation and back filling with argon. Toluene (1.0 mL) and water (1.0 mL) were added and the resulting brown suspension was flushed with nitrogen for 10 min. The reaction mixture was heated to 100° C. for 16 hours then filtered directly through a plug of dicalite. The filter cake was rinsed with EtOAc and the filtrate was washed with brine, dried (Na$_2$SO$_4$) and concentrated in vacuo. The residue was purified by preparative HPLC (mobile phase A: H$_2$O, B: CH$_3$CN with 0.05% Et$_3$N, C18 column) to afford the title compound (10 mg, 26%) as a colourless oil.

b) (11bR)-9-ethyl-2,3,4,6,7,11b-hexahydro-1H-pyrazino[2,1-a]isoquinoline hydrochloride To a stirred solution of tert-butyl (11bR)-9-ethyl-1,3,4,6,7,11b-hexahydropyrazino[2,1-a]isoquinoline-2-carboxylate (10 mg) in 1,4-dioxane (0.5 mL) was added a 4.0 m solution of HCl in dioxane (0.25 mL). The reaction mixture was stirred at 60° C. for 2 hours before being cooled to room temperature and stirred for further 6 hours. The resulting suspension was filtered through a sintered funnel. The collected hydrochloride salt was washed with further anhydrous diethyl ether then dried under high vacuum to afford the title compound (3.7 mg, 46%) as a white solid. MS (ISP): 217.1 ([M+H]$^+$).

Example 28

(11bR)-9-methyl-2,3,4,6,7,11b-hexahydro-1H-pyrazino[2,1-a]isoquinoline

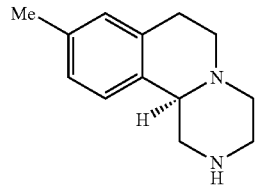 [SMILES: Cc1ccc2c(c1)CCN1CCNC[C@@H]21]

The title compound was obtained in analogy to Example 27 using methylboronic acid (CAS 13061-96-6) in place of ethylboronic acid in step (a). Off-white solid. MS (ISP): 203.1 ([M+H]$^+$).

Example 29

(11bR)-9-cyclopropyl-2,3,4,6,7,11b-hexahydro-1H-pyrazino[2,1-a]isoquinoline

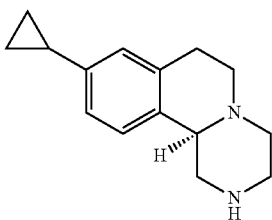 [SMILES: c1cc2c(cc1C1CC1)CCN1CCNC[C@@H]21]

The title compound was obtained in analogy to Example 27 using cyclopropylboronic acid (CAS 411235-57-9) in place of ethylboronic acid in step (a). Off-white solid. MS (ISP): 229.1 ([M+H]$^+$).

Example 30

(11bR)-8-fluoro-2,3,4,6,7,11b-hexahydro-1H-pyrazino[2,1-a]isoquinoline

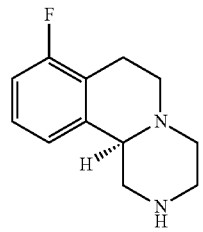 [SMILES: Fc1cccc2c1CCN1CCNC[C@@H]21]

a) 2-(3-bromo-2-fluorophenyl)ethanamine

To a stirred solution of 2-(3-bromo-2-fluoro-phenyl)acetonitrile (10 g, 44.4 mmol, CAS 874285-03-7) in THF (100 mL) was added borane-tetrahydrofuran complex 1.0 M in THF (88.8 mL, 88.8 mmol) at 0° C. The mixture was stirred at room temperature for 1 hour then heated to reflux overnight. The reaction mixture was then re-cooled to 0° C. and MeOH (50 mL) was added. The mixture was heated to reflux for 90 min. The solvent was removed under vacuum and the residue was partitioned between EtOAc and aqueous 1.0 M HCl. The aqueous phase was made basic with aqueous 1.0 M NaOH then extracted with EtOAc. Organic layers were washed with saturated brine, dried (Na$_2$SO$_4$) and concentrated in vacuo to afford the title compound (9.1 g, 94%) as a viscous colorless oil which was used in the next step without further purification.

b) N-(3-bromo-2-fluorophenethyl)-2-chloroacetamide

To a suspension of 2-(3-bromo-2-fluorophenyl)ethanamine (9.1 g, 41.7 mmol) and NaHCO$_3$ (3.68 g, 43.8 mmol) in dichloromethane (35 mL) was added dropwise chloroacetyl chloride (4.01 mL, 50.1 mmol) at 0° C. during 30 min. The reaction mixture was allowed to warm to room temperature overnight, before being quenched by slow addition of water at 0° C. The organic layer was separated, and washed successively with 10% aqueous HCl solution and brine, dried (Na$_2$SO$_4$), filtered and concentrated in vacuo to afford the title compound (7.5 g) as a crystalline light yellow solid which was used in the next step without further purification.

c) N-(3-bromo-2-fluorophenethyl)-2-(2,2-dimethoxyethylamino)acetamide

To a solution of N-(3-bromo-2-fluorophenethyl)-2-chloroacetamide (7.53 g, 25.6 mmol) in toluene (20 mL) was added aminoacetaldehyde dimethyl acetal (5.64 mL, 51.1 mmol, CAS 22483-09-6) and the mixture was heated to reflux for 2 hours. After cooling to room temperature, the solvent was evaporated and the residue partitioned between EtOAc and water. The phases were separated and the organic layer was dried over Na$_2$SO$_4$ and concentrated in vacuo to afford the title compound (9.0 g) as an orange oil which was used in the next step without further purification.

d) 9-bromo-8-fluoro-1,2,3,6,7,11b-hexahydropyrazino[2,1-a]isoquinolin-4-one

To a solution of N-(3-bromo-2-fluorophenethyl)-2-(2,2-dimethoxyethylamino)acetamide (8.0 g, 22 mmol) in CH$_2$Cl$_2$ (20 mL) was added dropwise sulfuric acid (7.63 mL, 143 mmol) at 0-5° C. The reaction mixture was allowed to warm up to room temperature for 1 hour before being poured into ice-water. The pH was adjusted to 12 by addition of aqueous NaOH (20 wt. %) while cooling. The water phase was extracted with CH$_2$Cl$_2$ twice. The combined organic extracts were washed with brine, dried (Na$_2$SO$_4$), filtered and concentrated in vacuo. The residue was purified by flash chromatography (silica gel, gradient 5% to 10% MeOH in CH$_2$Cl$_2$) to afford the title compound (2.68 g, 41% yield) as a light brown solid. MS (ISP): 301.0 ([{$^{81}$Br}M+H]$^+$), 299.0 ([{$^{79}$Br}M+H]$^+$)

e) tert-butyl 9-bromo-8-fluoro-4-oxo-3,4,6,7-tetrahydro-1H-pyrazino[2,1-a]isoquinoline-2(11bH)-carboxylate To a stirred solution of 9-bromo-8-fluoro-1,2,3,6,7,11b-hexahydropyrazino[2,1-a]isoquinolin-4-one (2.8 g, 9.36 mmol) and Et$_3$N (4.57 mL, 32.8 mmol) in CH$_2$Cl$_2$ (60 mL) was added Boc$_2$O (2.45 g, 11.2 mmol) and the mixture was stirred at room temperature for 16 hours. The reaction mixture was partitioned between aqueous citric (10 wt. %) acid and CH$_2$Cl$_2$. The layers were separated and the organic phase was washed with saturated aqueous NaHCO$_3$, dried (Na$_2$SO$_4$) and concentrated in vacuo. The residue was purified by flash column chromatography (silica gel; gradient: 0% to 40% EtOAc in heptane) to afford the title compound (3.51 g, 94%) as viscous yellow oil.

f) tert-butyl (11bR)-9-bromo-8-fluoro-4-oxo-3,6,7,11b-tetrahydro-1H-pyrazino[2,1-a]isoquinoline-2-carboxylate & tert-butyl (11bS)-9-bromo-8-fluoro-4-oxo-3,6,7,11b-tetrahydro-1H-pyrazino[2,1-a]isoquinoline-2-carboxylate The enantiomers of (RS)-tert-butyl 9-bromo-10-fluoro-4-oxo-3,4,6,7-tetrahydro-1H-pyrazino[2,1-a]isoquinoline-2(11bH)-carboxylate (3.64 g) were separated using SFC (column: Chiralpak AD-H, 250×20 mm; eluent: 40% methanol+0.1% Et$_2$NH in 60% CO$_2$) affording:
(+)-tert-butyl (11bS)-9-bromo-10-fluoro-4-oxo-3,6,7,11b-tetrahydro-1H-pyrazino[2,1-a]isoquinoline-2-carboxylate (1.14 g, light orange solid), retention time=5.20 min
(−)-tert-butyl (11bR)-9-bromo-8-fluoro-4-oxo-3,6,7,11b-tetrahydro-1H-pyrazino[2,1-a]isoquinoline-2-carboxylate (0.790 g, light orange solid), retention time=6.15 min g) tert-butyl (11bR)-9-bromo-8-fluoro-1,3,4,6,7,11b-hexahydropyrazino[2,1-a]isoquinoline-2-carboxylate To a stirred solution of tert-butyl (11bR)-9-bromo-8-fluoro-4-oxo-3,6,7,11b-tetrahydro-1H-pyrazino[2,1-a]isoquinoline-2-carboxylate (790 mg, 1.98 mmol) in THF (31 mL) was added borane-tetrahydrofuran complex 1.0 M in THF (11.9 mL, 11.9 mmol) and the mixture was stirred at room temperature for 16 hours. The reaction mixture was then poured into saturated aqueous NaHCO$_3$ and extracted twice with EtOAc. The combined organic extracts were washed with saturated brine, dried (Na$_2$SO$_4$) and concentrated in vacuo. The residue was purified by flash column chromatography (silica gel; gradient: 0% to 30% EtOAc in heptane) to afford the title compound (240 mg, 75%) as a light yellow foam. MS (ISP): 388.1 ([{$^{81}$Br}M+H]$^+$), 386.1 ([{$^{79}$Br}M+H]$^+$).

h) (11bR)-8-fluoro-2,3,4,6,7,11b-hexahydro-1H-pyrazino[2,1-a]isoquinoline 2,2,2-trifluoroacetic acid To a stirred solution of tert-butyl (11bR)-9-bromo-8-fluoro-1,3,4,6,7,11b-hexahydropyrazino[2,1-a]isoquinoline-2-carboxylate (50 mg, 0.130 mmol) in methanol (3 mL) was added 10 wt. % Pd/C (13.8 mg, 0.0013 mmol). The resulting black suspension was degassed by alternative evacuation and back filling with a stream of hydrogen (balloon) for three times. The mixture was stirred for 17 hours at room temperature under hydrogen atmosphere then filtered through a pad of dicalite. The filter cake was rinsed with EtOAc and the filtrate was concentrated in vacuo. The residue was dissolved in CH$_2$Cl$_2$ (4.0 mL) and TFA (2.0 mL) was added. The resulting yellow solution was stirred at room temperature for 2 hours before all volatiles were removed under high vacuum to afford the title compound (24 mg, 58%) as a light yellow oil.

Example 31

(11bS)—N-[6-chloro-2-(trifluoromethyl)pyrimidin-4-yl]-8-fluoro-2,3,4,6,7,11b-hexahydro-1H-pyrazino[2,1-a]isoquinolin-9-amine

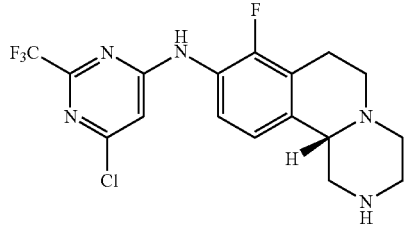 [SMILES: Fc1c(Nc2cc(Cl)nc(C(F)(F)F)n2)ccc2c1CCN1CCNC[C@H]21]

a) tert-butyl (11bS)-9-(benzhydrylideneamino)-8-fluoro-1,3,4,6,7,11b-hexahydropyrazino[2,1-a]isoquinoline-2-carboxylate A screw-cap vial was charged with tert-butyl (11bS)-9-bromo-8-fluoro-4-oxo-3,6,7,11b-tetrahydro-1H-pyrazino[2,1-a]isoquinoline-2-carboxylate (250 mg, 0.649 mmol), benzophenone imine (0.218 ml, 1.3 mmol), (rac)-2,2'-bis(diphenylphosphino)-1,1'-binaphthyl (40.4 mg, 0.065 mmol), tris(dibenzylideneacetone)dipalladium(0) (17.8 mg, 19.5 µmol) and sodium tert-butoxide (99.8 mg, 1.04 mmol). The vial was then degassed by alternative evacuation and back filling with argon. Toluene (1.5 mL) was added and the resulting mixture was flushed with a stream of argon for 10 min. The reaction mixture was heated to 90° C. in an oil bath for 3 hours then filtered directly through a plug of dicalite. The filter cake was rinsed with EtOAc and the filtrate was washed with brine, dried (Na$_2$SO$_4$) and concentrated in vacuo. The residue was purified by flash column chromatography (silica gel; gradient: 0% to 40% EtOAc in heptane) to afford the title compound (186 mg, 59%) as a yellow oil. MS (ISP): 486.3 ([M+H]$^+$).

b) tert-butyl (11bS)-9-amino-8-fluoro-1,3,4,6,7,11b-hexahydropyrazino[2,1-a]isoquinoline-2-carboxylate To a stirred solution of tert-butyl (11bS)-9-(benzhydrylideneamino)-8-fluoro-1,3,4,6,7,11b-hexahydropyrazino[2,1-a]isoquinoline-2-carboxylate (186 mg, 0.383 mmol) in methanol (5 mL) was added sodium acetate (94.3 mg, 1.15 mmol), hydroxylamine hydrochloride (58.6 mg, 0.843 mmol) and the reaction mixture was stirred at 50° C. overnight. The reaction mixture was then cooled to room temperature and partitioned between 1.0 M aqueous NaOH and EtOAc. The layers were separated and the organic layer was dried over Na₂SO₄ and concentrated in vacuo. The residue was purified by flash column chromatography (silica gel; gradient: 5% to 25% EtOAc+10% MeOH in heptane) to afford the title compound (101 mg, 82%) as a white foam. MS (EI): 322.2 ([M+H]$^+$).

c) tert-butyl (11bS)-9-[[6-chloro-2-(trifluoromethyl)pyrimidin-4-yl]amino]-8-fluoro-1,3,4,6,7,11b-hexahydropyrazino[2,1-a]isoquinoline-2-carboxylate To a stirred solution of tert-butyl (11bS)-9-amino-8-fluoro-1,3,4,6,7,11b-hexahydropyrazino[2,1-a]isoquinoline-2-carboxylate (30 mg, 0.093 mmol) in DMA (1.0 mL) and N,N-diisopropylethylamine (24.5 µl, 140 µmol) was added 4,6-dichloro-2-(trifluoromethyl)pyrimidine (26.3 mg, 0.093 mmol, CAS 705-24-8) and the mixture was stirred at 100° C. overnight. The reaction mixture was then poured into water and extracted twice with EtOAc. The combined organic layers were washed with brine, dried (Na₂SO₄) and concentrated in vacuo. The residue was purified by flash column chromatography (silica gel; gradient: 0% to 100% EtOAc in heptane) to afford the title compound (10 mg, 24%) as a white solid. MS (ISP): 504.2 ([{$^{37}$Cl}M+H]$^+$), 502.2 ([{$^{35}$Cl}M+H]$^+$).

b) (11bS)—N-[6-chloro-2-(trifluoromethyl)pyrimidin-4-yl]-8-fluoro-2,3,4,6,7,11b-hexahydro-1H-pyrazino[2,1-a]isoquinolin-9-amine hydrochloride To a stirred solution of tert-butyl (11bS)-9-[[6-chloro-2-(trifluoromethyl)pyrimidin-4-yl]amino]-8-fluoro-1,3,4,6,7,11b-hexahydropyrazino[2,1-a]isoquinoline-2-carboxylate (10 mg) in 1,4-dioxane (0.5 mL) was added a 4.0 M solution of HCl in dioxane (0.25 mL). The reaction mixture was stirred at 60° C. for 2 hours before being cooled to room temperature and stirred for further 6 hours. The resulting suspension was filtered through a sintered funnel. The collected hydrochloride salt was washed with further anhydrous diethyl ether then dried under high vacuum to afford the title compound (10 mg, 57%) as a light yellow solid. MS (ISP): 404.1 ([{$^{37}$Cl}M+H]$^+$), 402.1 ([{$^{35}$Cl}M+H]$^+$).

Example 32

N-[(11bR)-8-fluoro-2,3,4,6,7,11b-hexahydro-1H-pyrazino[2,1-a]isoquinolin-9-yl]-2-(trifluoromethyl)pyridine-4-carboxamide

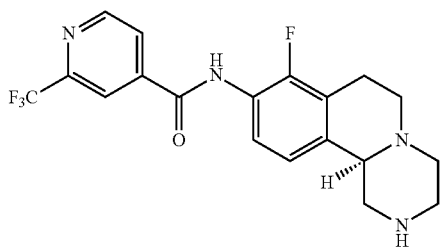 [SMILES: O=C(Nc1ccc2c(c1F)CCN1CCNC[C@@H]21)c1ccnc(C(F)(F)F)c1]

The title compound was obtained in analogy to Example 1 using tert-butyl (11bR)-9-amino-8-fluoro-1,3,4,6,7,11b-hexahydropyrazino[2,1-a]isoquinoline-2-carboxylate in place of tert-butyl (11bR)-9-amino-1,3,4,6,7,11b-hexahydropyrazino[2,1-a]isoquinoline-2-carboxylate in step (i). Light yellow solid. MS (ISP): 395.1 ([M+H]$^+$).

Example 33

(11bR)—N-(5-cyclopropylpyrimidin-2-yl)-8-fluoro-2,3,4,6,7,11b-hexahydro-1H-pyrazino[2,1-a]isoquinolin-9-amine

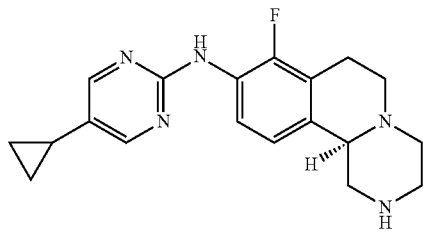 [SMILES: Fc1c(Nc2ncc(C3CC3)cn2)ccc2c1CCN1CCNC[C@@H]21]

The title compound was obtained in analogy to Example 7 using tert-butyl (11bR)-9-amino-8-fluoro-1,3,4,6,7,11b-hexahydropyrazino[2,1-a]isoquinoline-2-carboxylate in place of tert-butyl (11bR)-9-amino-1,3,4,6,7,11b-hexahydropyrazino[2,1-a]isoquinoline-2-carboxylate and 2-chloro-5-cyclopropylpyrimidine (CAS 166740-44-9) in place of 2-chloro-5-(trifluoromethyl)pyrazine in step (a). White solid. MS (ISP): 340.2 ([M+H]$^+$).

Example 34

(11bR)—N-[6-chloro-2-(trifluoromethyl)pyrimidin-4-yl]-8-fluoro-2,3,4,6,7,11b-hexahydro-1H-pyrazino[2,1-a]isoquinolin-9-amine

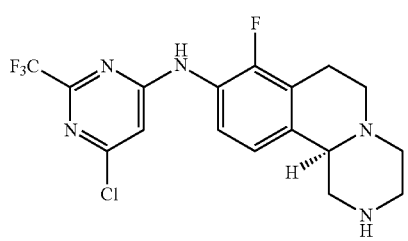 [SMILES: Fc1c(Nc2cc(Cl)nc(C(F)(F)F)n2)ccc2c1CCN1CCNC[C@@H]21]

The title compound was obtained in analogy to Example 31 using tert-butyl (11bR)-9-bromo-8-fluoro-4-oxo-3,6,7,11b-tetrahydro-1H-pyrazino[2,1-a]isoquinoline-2-carboxylate in place of tert-butyl (11bS)-9-bromo-8-fluoro-4-oxo-3,6,7,11b-tetrahydro-1H-pyrazino[2,1-a]isoquinoline-2-carboxylate in step (a). White solid. MS (ISP): 504.2 ([{$^{37}$Cl}M+H]$^+$), 502.2 ([{$^{35}$Cl}M+H]$^+$).

Example 35

(R)-1-(2,3,4,6,7,11b-hexahydro-1H-pyrazino[2,1-a]isoquinolin-9-yl)-3-(4-(trifluoromethyl)phenyl)urea

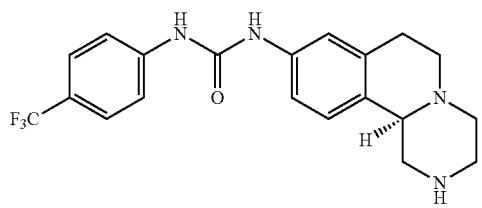 [SMILES: O=C(Nc1ccc(C(F)(F)F)cc1)Nc1ccc2c(c1)CCN1CCNC[C@@H]21]

a) tert-butyl (11bR)-9-[[4-(trifluoromethyl)phenyl]carbamoylamino]-1,3,4,6,7,11b-hexahydropyrazino[2,1-a]isoquinoline-2-carboxylate To a stirred solution of tert-butyl (11bR)-9-amino-1,3,4,6,7,11b-hexahydropyrazino[2,1-a]isoquinoline-2-carboxylate (30 mg, 98.9 µmol) in THF (2 ml) was added 4-(trifluoromethyl)phenyl isocyanate (22.3 mg, 0.119 mmol, CAS 1548-13-6). The reaction mixture was stirred at room temperature for 1 hour before all volatiles were evaporated. The crude residue was purified by flash column chromatography (silica gel; gradient: 0% to 50% EtOAc in heptane) to afford the title compound (27.2 mg, 56%) as a white solid. MS (ISP): 491.2 ([M+H]$^+$).

b) (R)-1-(2,3,4,6,7,11b-hexahydro-1H-pyrazino[2,1-a]isoquinolin-9-yl)-3-(4-(trifluoromethyl)phenyl)urea hydrochloride To a stirred solution of tert-butyl (11bR)-9-[[4-(trifluoromethyl)phenyl]carbamoylamino]-1,3,4,6,7,11b-hexahydropyrazino[2,1-a]isoquinoline-2-carboxylate (27.2 mg) in 1,4-dioxane (0.5 mL) was added a 4.0 m solution of HCl in 1,4-dioxane (0.25 mL). The reaction mixture was stirred at 60° C. for 2 hours before being cooled to room temperature and stirred for further 6 hours. The resulting suspension was filtered through a sintered funnel. The collected hydrochloride salt was washed with further anhydrous diethyl ether then dried under high vacuum to afford the title compound (13.7 mg, 40%) as a white solid. MS (ISP): 391.2 ([M+H]$^+$).

Example 36

(R)-1-(2,3,4,6,7,11b-hexahydro-1H-pyrazino[2,1-a]isoquinolin-9-yl)-3-(4-methoxyphenyl)urea

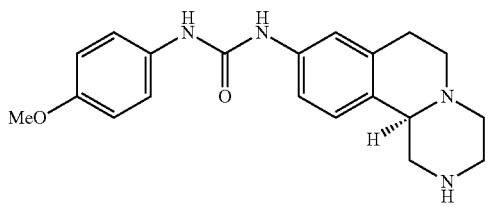 [SMILES: COc1ccc(NC(=O)Nc2ccc3c(c2)CCN2CCNC[C@@H]32)cc1]

The title compound was obtained in analogy to Example 35 using 4-(methoxy)phenyl isocyanate (CAS 5416-93-3) in place of 4-(trifluoromethyl)phenyl isocyanate in step (a). Off-white solid. MS (ISP): 353.2 ([M+H]$^+$).

Example 37

N-[(11R)-2,3,4,6,7,11-hexahydro-1H-pyrazino[2,1-a]isoquinolin-9-yl]-3-cyclopropyl-1,2,4-oxadiazol-5-amine

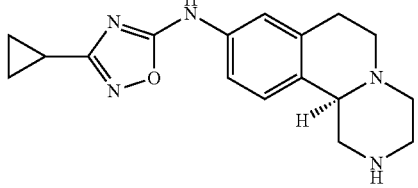

The title compound was obtained in analogy to Example 5 using 5-chloro-3-cyclopropyl-1,2,4-oxadiazole in place of 4-chloro-2-(trifluoromethyl)pyrimidine in step (a). Orange solid. MS (ISP): 312.2 ([M+H]$^+$).

Example 38

(R)—N-(2,3,4,6,7,11b-hexahydro-1H-pyrazino[2,1-a]isoquinolin-9-yl)-6-methyl-2-(trifluoromethyl)pyrimidine-4-carboxamide

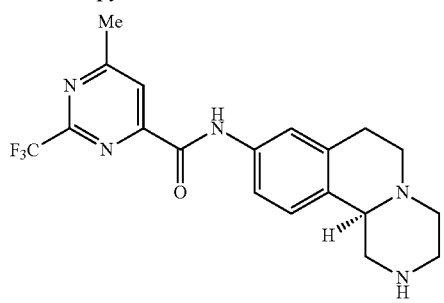

The title compound was obtained in analogy to Example 1 using 6-methyl-2-(trifluoromethyl) pyrimidine-4-carboxylic acid (CAS 945717-59-9) in place of 2-(trifluoromethyl)pyridine-4-carboxylic acid in step (i). Yellow solid. MS (ISP): 392.2 ([M+H]$^+$).

Example 39

(R)—N-(2,3,4,6,7,11b-hexahydro-1H-pyrazino[2,1-a]isoquinolin-9-yl)-3-isopropyl-1-methyl-1H-pyrazole-5-carboxamide

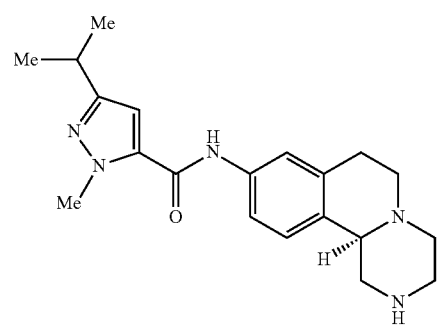 [SMILES: CC(C)c1cc(C(=O)Nc2ccc3c(c2)CCN2CCNC[C@@H]32)n(C)n1]

The title compound was obtained in analogy to Example 1 using 5-isopropyl-2-methyl-pyrazole-3-carboxylic acid (CAS 78208-73-8) in place of 2-(trifluoromethyl)pyridine-4-carboxylic acid in step (i). Brown oil. MS (ISP): 354.2 ([M+H]$^+$).

Example 40

(R)—N-(2,3,4,6,7,11b-hexahydro-1H-pyrazino[2,1-a]isoquinolin-9-yl)-3-methyl-1,2,4-thiadiazol-5-amine

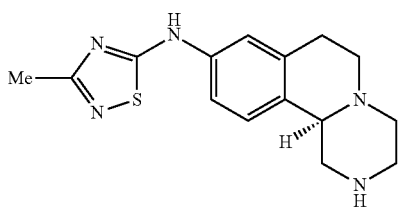 [SMILES: Cc1nsc(Nc2ccc3c(c2)CCN2CCNC[C@@H]32)n1]

The title compound was obtained in analogy to Example 5 using 5-bromo-3-methyl-1,2,4-thiadiazole (CAS 54681-68-4) in place of 4-chloro-2-(trifluoromethyl)pyrimidine in step (a). Orange solid. MS (ISP): 302.2 ([M+H]$^+$).

Example 41

(R)-3-ethyl-N-(2,3,4,6,7,11b-hexahydro-1H-pyrazino[2,1-a]isoquinolin-9-yl)-4-methyl-1H-pyrazole-5-carboxamide

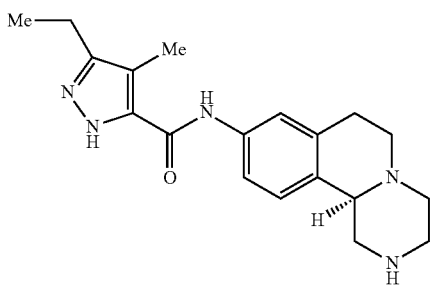 [SMILES: CCc1n[nH]c(C(=O)Nc2ccc3c(c2)CCN2CCNC[C@@H]32)c1C]

The title compound was obtained in analogy to Example 1 using 3-ethyl-4-methyl-1H-pyrazole-5-carboxylic acid (CAS 1094347-64-4) in place of 2-(trifluoromethyl)pyridine-4-carboxylic acid in step (i). White solid. MS (ISP): 340.2 ([M+H]$^+$).

Example 42

(11 bR)—N-(6-chloro-3-pyridyl)-2,3,4,6,7,11 b-hexahydro-1H-pyrazino[2,1-a]isoquinoline-9-carboxamide

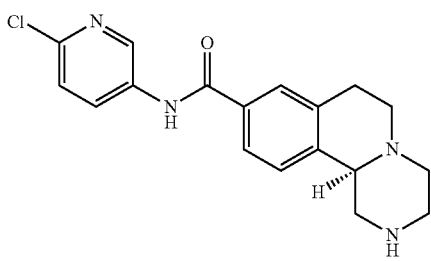 [SMILES: O=C(Nc1ccc(Cl)nc1)c1ccc2c(c1)CCN1CCNC[C@@H]21]

a) O-tert-butyl O-methyl (11bR)-1,3,4,6,7,11b-hexahydropyrazino[2,1-a]isoquinoline-2,9-dicarboxylate To a stirred solution of tert-butyl (11bR)-9-bromo-1,3,4,6,7,11b-hexahydropyrazino[2,1-a]isoquinoline-2-carboxylate (218 mg, 0.594 mmol, Eq: 1.00) and triethylamine (601 mg, 827 μl 5.94 mmol, Eq: 10) in a 1:1 mixture of DMSO and methanol (4 mL) were added 1,3-bis(diphenylphosphino)propane (49.0 mg, 119 μmol, CAS 6737-42-4) and Pd(OAc)$_2$ (26.7 mg, 119 μmol). The resulting black suspension was purged by evacuation and then back filled with stream of $CO_{(g)}$ (balloon) for three times then heated to 80° C. for 16 hours under CO atmosphere. The reaction mixture was then poured into water and extracted twice with EtOAc. The combined organic layers were washed with saturated brine, dried (Na$_2$SO$_4$) and concentrated in vacuo. The residue was purified by flash column chromatography (silica gel; gradient: 0% to 40% EtOAc in heptane) to afford the title compound (121 mg, 59%) as a light yellow oil. MS (ISP): 347.2 ([M+H]$^+$).

b) (11bR)-2-tert-butoxycarbonyl-1,3,4,6,7,11b-hexahydropyrazino[2,1-a]isoquinoline-9-carboxylic acid To a stirred solution of O-tert-butyl O-methyl (11bR)-1,3,4,6,7,11b-hexahydropyrazino[2,1-a]isoquinoline-2,9-dicarboxylate (196 mg, 0.566 mmol) in a 1:1 mixture of THF and water (3.0 mL) was added LiOH (20.7 mg, 0.885 mmol). The reaction mixture was stirred at room temperature for 16 hours. The pH was adjusted to 3-4 by dropwise addition of aqueous 1.0 m HCl. The water phase was extracted with CH$_2$Cl$_2$ twice and the organic layers were dried (Na$_2$SO$_4$) and concentrated in vacuo to afford the title compound as a yellow oil (169 mg, 90%) which was used in the next step without further purification. MS (ISP): 331.2, ([M−H]$^-$).

c) tert-butyl (11bR)-9-[(6-chloro-3-pyridyl)carbamoyl]-1,3,4,6,7,11b-hexahydropyrazino[2,1-a]isoquinoline-2-carboxylate To a stirred solution of (11bR)-2-tert-butoxycarbonyl-1,3,4,6,7,11b-hexahydropyrazino[2,1-a]isoquinoline-9-carboxylic acid (30 mg, 0.090 mmol) and 6-chloropyridin-3-amine (11.6 mg, 0.090 mmol) in 1,4-dioxane (0.5 mL) was added a 50 wt. % solution of 1-propylphosphonic acid cyclic anhydride in EtOAc (114 mg, 107 μl, 0.180 mmol, CAS 68957-94-8). The reaction mixture was stirred at room temperature for 16 hours. The reaction crude was purified directly by preparative HPLC (mobile phase A: H$_2$O, B: CH$_3$CN with 0.05% Et$_3$N, C18 column) to afford the title compound (18 mg, 45%) as a colorless oil. MS (ISP): 445.1 ([{$^{37}$Cl}M+H]$^+$), 443.2 ([{$^{35}$Cl}M+H]$^+$).

d) (11bR)—N-(6-chloro-3-pyridyl)-2,3,4,6,7,11b-hexahydro-1H-pyrazino[2,1-a]isoquinoline-9-carboxamide hydrochloride To a stirred solution of tert-butyl (11bR)-9-[(6-chloro-3-pyridyl)carbamoyl]-1,3,4,6,7,11b-hexahydropyrazino[2,1-a]isoquinoline-2-carboxylate (18 mg) in 1,4-dioxane (0.5 mL) was added a 4.0 m solution of HCl in dioxane (0.25 mL). The reaction mixture was stirred at 60° C. for 2 hours before being cooled to room temperature and stirred for further 6 hours. The resulting suspension was filtered through a sintered funnel. The collected hydrochloride salt was washed with further anhydrous diethyl ether then dried

Example 43

(11bR)—N-[[3-(trifluoromethyl)phenyl]methyl]-2,3,4,6,7,11b-hexahydro-1H-pyrazino[2,1-a]isoquinoline-9-carboxamide

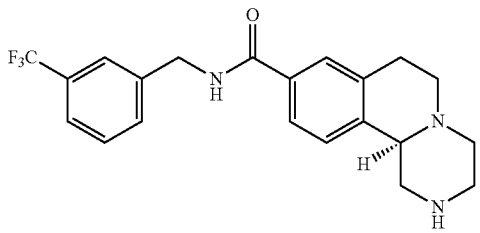 [SMILES: O=C(NCc1cccc(C(F)(F)F)c1)c1ccc2c(c1)CCN1CCNC[C@@H]21]

The title compound was obtained in analogy to example 42 using 3-(trifluoromethyl) benzylamine (CAS 2740-83-2) in place of 6-chloropyridin-3-amine in step (c). Light yellow solid. MS (ISP): 390.2 ([M+H]$^+$).

Example 44

(11bR)—N-(4-chlorophenyl)-2,3,4,6,7,11b-hexahydro-1H-pyrazino[2,1-a]isoquinoline-9-carboxamide

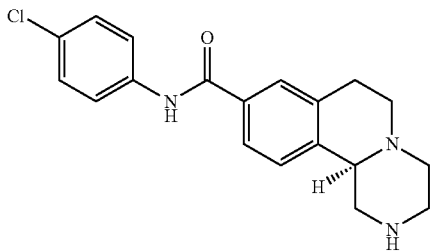 [SMILES: O=C(Nc1ccc(Cl)cc1)c1ccc2c(c1)CCN1CCNC[C@@H]21]

The title compound was obtained in analogy to Example 42 using 4-chloroaniline (CAS 106-47-8) in place of 6-chloropyridin-3-amine in step (c). White solid. MS (ISP): 344.2 ([{$^{37}$Cl}M+H]$^+$), 342.2 ([{$^{35}$Cl}M+H]$^+$).

Example 45

(11bR)—N-(6-methoxy-3-pyridyl)-2,3,4,6,7,11b-hexahydro-1H-pyrazino[2,1-a]isoquinoline-9-carboxamide

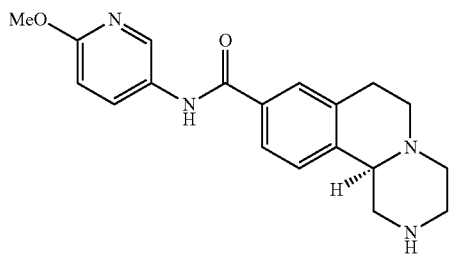 [SMILES: COc1ccc(NC(=O)c2ccc3c(c2)CCN2CCNC[C@@H]32)cn1]

The title compound was obtained in analogy to Example 42 using 6-methoxypyridin-3-amine (CAS 6628-77-9) in place of 6-chloropyridin-3-amine in step (c). Pink solid. MS (ISP): 337.3 ([M–H]$^-$).

Example 46

(11bR)—N-(2-chloropyrimidin-5-yl)-2,3,4,6,7,11b-hexahydro-1H-pyrazino[2,1-a]isoquinoline-9-carboxamide

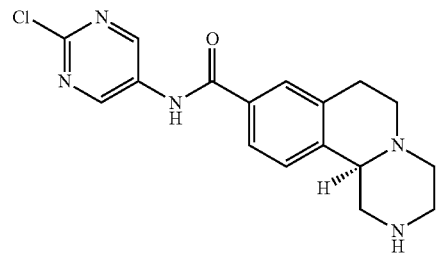 [SMILES: O=C(Nc1cnc(Cl)nc1)c1ccc2c(c1)CCN1CCNC[C@@H]21]

The title compound was obtained in analogy to Example 42 using 2-chloropyrimidin-5-amine (CAS 56621-90-0) in place of 6-chloropyridin-3-amine in step (c). Light yellow solid. 344.2 ([{$^{37}$Cl}M+H]$^+$), 346.2 ([{$^{35}$Cl}M+H]$^+$).

Example 47

(11bR)-2,3,4,6,7,11b-hexahydro-1H-pyrazino[2,1-a]isoquinolin-9-amine

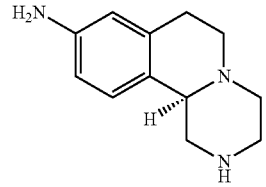 [SMILES: Nc1ccc2c(c1)CCN1CCNC[C@@H]21]

To a stirred solution of tert-butyl (11bR)-9-amino-1,3,4,6,7,11b-hexahydropyrazino[2,1-a]isoquinoline-2-carboxylate (172 mg, 0.567 mmol) in 1,4-dioxane (3.0 mL) was added a 4.0 m solution of HCl in dioxane (1.5 mL). The reaction mixture was stirred at 60° C. for 2 hours before being cooled to room temperature and stirred for further 16 hours. The resulting suspension was filtered through a sintered funnel. The collected dihydrochloride salt was washed with further anhydrous diethyl ether then dried under high vacuum to afford the title compound (119 mg, 76%) as a white solid. MS (ISP): 204.1 ([M+H]$^+$).

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer.

PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Radioligand Binding Assay on Rat TAAR1
Membrane Preparation and Radioligand Binding.

HEK-293 cells stably expressing rat TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant ($K_d$) was determined via a saturation curve. The TAAR1 radioligand $^3$[H]—(S)-4-[(ethyl-phenyl-amino)-methyl]-4,5-dihydro-oxazol-2-ylamine (described in WO 2008/098857) was used at a concentration equal to the calculated $K_d$ value, that was usually around 2.3 nM, resulting in the binding of approximately 0.2% of the radioligand and a specific binding representing approximately 85% of the total binding. Nonspecific binding was defined as the amount of $^3$[H]—(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 □µl/well) were transferred into a 96 deep well plate (TreffLab), and 180 µl of HEPES-NaOH (20 mM, pH 7.4) containing $MgCl_2$ (10 mM) and $CaCl_2$ (2 mM) (binding buffer), 300 µl of the radioligand $^3$[H]—(S)-4-[(ethyl-phenyl-amino)-methyl]-4,5-dihydro-oxazol-2-ylamine at a concentration of 3.3× $K_d$ in nM and 500 µl of the membranes (resuspended at 50 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the radioactivity counted using a TopCount Microplate Scintillation Counter (Packard Instrument Company).

Radioligand Binding Assay on Mouse TAAR1
Membrane Preparation and Radioligand Binding.

HEK-293 cells stably expressing mouse TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant ($K_d$) was determined via a saturation curve. The TAAR1 radioligand $^3$[H]—(S)-4-[(ethyl-phenyl-amino)-methyl]-4,5-dihydro-oxazol-2-ylamine (described in WO 2008/098857) was used at a concentration equal to the calculated $K_d$ value, that was usually around 0.7 nM, resulting in the binding of approximately 0.5% of the radioligand and a specific binding representing approximately 70% of the total binding. Nonspecific binding was defined as the amount of $^3$[H]—(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 □µl/well) were transferred into a 96 deep well plate (TrefflLab), and 180 µl of HEPES-NaOH (20 mM, pH 7.4) containing $MgCl_2$ (10 mM) and $CaCl_2$ (2 mM) (binding buffer), 300 µl of the radioligand $^3$[H]—(S)-4-[(ethyl-phenyl-amino)-methyl]-4,5-dihydro-oxazol-2-ylamine at a concentration of 3.3× $K_d$ in nM and 500 µl of the membranes (resuspended at 60 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the radioactivity counted using a TopCount Microplate Scintillation Counter (Packard Instrument Company).

The compounds show a $K_i$ value in mouse or rat on TAAR1 (in µM) as shown in the table below.

| Example | Ki (µM) mouse/rat |
|---|---|
| 1 | 0.121/0.1988 |
| 2 | 0.18/0.1292 |
| 3 | 0.0096/0.0562 |
| 4 | 0.1889/0.1395 |
| 5 | 0.0354/0.0151 |
| 6 | 0.0374/0.0195 |
| 7 | 0.0329/0.0356 |
| 8 | 0.0075 |
|  | 0.0063 |

-continued

| Example | Ki (μM) mouse/rat |
|---|---|
| 9 | 0.0144 |
|   | 0.0142 |
| 10 | 0.1887 |
|   | 0.1913 |
| 11 | 1.183 |
|   | 0.9043 |
| 12 | 0.2186 |
|   | 1.984 |
| 13 | 0.0078 |
|   | 0.0119 |
| 14 | 0.0066 |
|   | 0.0192 |
| 15 | 0.0605 |
|   | 0.2477 |
| 16 | 0.1746 |
|   | 1.498 |
| 17 | 0.2605 |
|   | 0.6233 |
| 18 | 0.0439 |
|   | 0.0092 |
| 19 | 0.0231 |
|   | 0.0076 |
| 20 | 0.0364 |
|   | 0.0112 |
| 21 | 0.0264 |
|   | 0.0134 |
| 22 | 0.5367 |
|   | 3.9244 |
| 23 | 0.165 |
|   | 0.4567 |
| 24 | 0.0599 |
|   | 0.0471 |
| 25 | 0.0349 |
|   | 0.0438 |
| 26 | 0.041 |
|   | 0.1539 |
| 27 | 0.2656 |
|   | 0.2878 |
| 28 | 0.2903 |
|   | 0.421 |
| 29 | 1.8149 |
|   | 0.8151 |
| 30 | 0.1761 |
|   | 0.2013 |
| 31 | 0.8345 |
|   | 1.7313 |
| 32 | 0.4435 |
|   | 7.6338 |
| 33 | 0.0677 |
|   | 0.1055 |
| 34 | 0.0795 |
|   | 0.2228 |
| 35 | 0.0025 |
|   | 0.0012 |
| 36 | 0.0101 |
|   | 0.023 |
| 37 | 0.0347 |
|   | 0.1984 |
| 38 | 0.2222 |
|   | 0.1571 |
| 39 | 1.0679 |
|   | 0.8691 |
| 40 | 0.2023 |
|   | 0.8262 |
| 41 | 0.1452 |
|   | 0.2878 |
| 42 | 0.0395 |
|   | 0.6824 |
| 43 | 0.0301 |
|   | 0.1366 |
| 44 | 0.0161 |
|   | 0.2736 |
| 45 | 0.2992 |
|   | >1.5 |
| 46 | 0.3091 |
|   | >1.5 |
| 47 | 1.1035 |
|   | >1.5 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety, attention deficit hyperactivity disorder (ADHD) and diabetes.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

We claim:

1. A compound of formula (I)

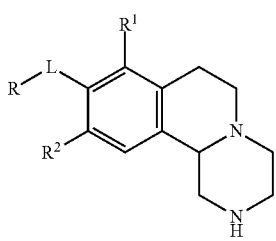

I wherein:
R$^1$ and R$^2$ are independently selected from hydrogen or halogen;
L is —C(O)NH—, —NHC(O)— or NHC(O)NH—;
R is hydrogen, lower alkyl, cycloalkyl, benzyl, phenyl or a five or six membered heteroaryl group, wherein phenyl and the heteroaryl groups are optionally substituted by one or two substituents, selected from halogen, lower alkyl, lower alkoxy, lower alkyl substituted by halogen, lower alkoxy substituted by halogen, cycloalkyl or di-lower alkyl amino; or, an enantiomer, a racemic mixture, or a mixture of enantiomers or a pharmaceutically suitable acid addition salt thereof.

2. The compound according to claim 1, in which L is —C(O)NH—.

3. The compound according to claim 1, which compound is:
N-[(11bR)-2,3,4,6,7,11b-hexahydro-1H-pyrazino[2,1-a]isoquinolin-9-yl]-2-(trifluoromethyl)pyridine-4-carboxamide;
N-[(11bR)-2,3,4,6,7,11b-hexahydro-1H-pyrazino[2,1-a]isoquinolin-9-yl]-4-chloro-benzamide;
N-[(11bR)-2,3,4,6,7,11b-hexahydro-1H-pyrazino[2,1-a]isoquinolin-9-yl]-2-(trifluoromethyl)pyrimidine-5-carboxamide;
N-[(11bS)-2,3,4,6,7,11b-hexahydro-1H-pyrazino[2,1-a]isoquinolin-9-yl]-4-chloro-benzamide;
N-[(11bS)-2,3,4,6,7,11b-hexahydro-1H-pyrazino[2,1-a]isoquinolin-9-yl]-2-(trifluoromethyl)pyridine-4-carboxamide;
N-[(11bS)-2,3,4,6,7,11b-hexahydro-1H-pyrazino[2,1-a]isoquinolin-9-yl]-2-(trifluoromethyl)pyrimidine-5-carboxamide;
N-[(11bR)-10-fluoro-2,3,4,6,7,11b-hexahydro-1H-pyrazino[2,1-a]isoquinolin-9-yl]-2-(trifluoro methyl)pyridine-4-carboxamide;
N-[(11bR)-8-fluoro-2,3,4,6,7,11b-hexahydro-1H-pyrazino[2,1-a]isoquinolin-9-yl]-2-(trifluoro methyl)pyridine-4-carboxamide;
(R)—N-(2,3,4,6,7,11b-hexahydro-1H-pyrazino[2,1-a]isoquinolin-9-yl)-6-methyl-2-(trifluoro methyl)pyrimidine-4-carboxamide;
(R)—N-(2,3,4,6,7,11b-hexahydro-1H-pyrazino[2,1-a]isoquinolin-9-yl)-3-isopropyl-1-methyl-1H-pyrazole-5-carboxamide; or,
(R)-3-ethyl-N-(2,3,4,6,7,11b-hexahydro-1H-pyrazino[2,1-a]isoquinolin-9-yl)-4-methyl-1H-pyrazole-5-carboxamide.

4. The compound according to claim 1 in which L is —NHC(O)—.

5. The compound according to claim 1 which compound is
(11bR)—N-(6-chloro-3-pyridyl)-2,3,4,6,7,11b-hexahydro-1H-pyrazino[2,1-a]isoquinoline-9-carboxamide;
(11bR)—N-[[3-(trifluoromethyl)phenyl]methyl]-2,3,4,6,7,11b-hexahydro-1H-pyrazino[2,1-a]isoquinoline-9-carboxamide;
(11bR)—N-(4-chlorophenyl)-2,3,4,6,7,11b-hexahydro-1H-pyrazino[2,1-a]isoquinoline-9-carboxamide;
(11bR)—N-(6-methoxy-3-pyridyl)-2,3,4,6,7,11b-hexahydro-1H-pyrazino[2,1-a]isoquinoline-9-carboxamide; or,
(11bR)—N-(2-chloropyrimidin-5-yl)-2,3,4,6,7,11b-hexahydro-1H-pyrazino[2,1-a]isoquinoline-9-carboxamide.

6. The compound according to claim 1 in which L is —NHC(O)NH—.

7. The compound according to claim 1, which compound is
(R)-1-(2,3,4,6,7,11b-hexahydro-1H-pyrazino[2,1-a]isoquinolin-9-yl)-3-(4-(trifluoromethyl)phenyl)urea; or,
(R)-1-(2,3,4,6,7,11b-hexahydro-1H-pyrazino[2,1-a]isoquinolin-9-yl)-3-(4-methoxyphenyl)urea.

8. A pharmaceutical composition comprising a compound according to claim 1 and at least one pharmaceutical acceptable excipient, carrier and/or adjuvant.

* * * * *